US010736288B2

(12) United States Patent
Haaring et al.

(10) Patent No.: US 10,736,288 B2
(45) Date of Patent: Aug. 11, 2020

(54) GENETIC BASIS FOR CUCUMBER FRUIT HAVING SMALL SEED CAVITY

(71) Applicant: RIJK ZWAAN ZAADTEELT EN ZAADHANDEL B.V., De Lier (NL)

(72) Inventors: Cornelis Haaring, De Lier (NL); Lena Johanna Huijbregts-Doorduin, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 15/798,487

(22) Filed: Oct. 31, 2017

(65) Prior Publication Data

US 2018/0054990 A1   Mar. 1, 2018

Related U.S. Application Data

(63) Continuation-in-part of application No. PCT/EP2016/064831, filed on Jun. 27, 2016.

(30) Foreign Application Priority Data

Jun. 26, 2015   (EP) .................................... 15174148

(51) Int. Cl.
| | | |
|---|---|---|
| *A01H 5/08* | (2018.01) | |
| *A01H 1/04* | (2006.01) | |
| *C12Q 1/6895* | (2018.01) | |
| *C07K 14/415* | (2006.01) | |

(52) U.S. Cl.
CPC ................. *A01H 5/08* (2013.01); *A01H 1/04* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 8,193,417 B2* | 6/2012 | Shetty | ...................... | A01H 5/08 435/410 |
| 2008/0229440 A1 | 9/2008 | Shetty | | |
| 2010/0287639 A1 | 11/2010 | Torres et al. | | |

OTHER PUBLICATIONS

Mauricio 2001 Nature vol. 2 370-381 (Year: 2001).*
International Search Report and Written Opinion of the International Searching Authority dated Sep. 7, 2016, which issued during prosecution of International Application No. PCT/EP2016/064831.
Johnny'S Selected Seeds "Corinto—Organic (F1) cucumber seed" retrieved Oct. 30, 2015 from http://www.johnnyseeds.com/p-8483-corinto.aspx.
Sun, et al. "Identification and comparative analysis of quantitative trait loci associated with parthenocarpy in processing cucumber" Plant Breeding, Jun. 2006, 125(3)281-287.

* cited by examiner

*Primary Examiner* — Brent T Page
(74) *Attorney, Agent, or Firm* — Duane Morris LLP; Thomas J. Kowalski; Deborah L. Lu

(57) ABSTRACT

The present invention relates to a parthenocarpic cucumber fruit (*Cucumis sativus* L.) having a small seed cavity. A parthenocarpic cucumber fruit (*Cucumis sativus* L.) having a small seed cavity has a lower total moisture content. Two QTLs have been identified that either alone or in combination lead to the phenotype of having a small seed cavity. The invention further relates to a cucumber plant comprising one of the QTLs or a combination of both QTLs, which cucumber plant is capable of producing parthenocarpic fruits that have a small seed cavity. The invention also relates to markers for identifying the QTLs.

26 Claims, 10 Drawing Sheets
Specification includes a Sequence Listing.

Fig. 1A

SEQ ID No. 1 - (B) polymorphism SNP on position 71
ACTGAGACATGCAGGCAGACTTGCGAAGATMTAGACTCGAGCTTTATCATTGGCCTTTATTCAGCAGTATA
CCTAACAGCTTGGTATGCATTACGAGCAGGGGCTGTA SEQ ID No. 2 - (B) polymorphism SNP on position 154
CTGCAGCCAACTATAAATGATATCACTACCACCACGGTTGAGTGAGCACGGAGGGACTGACGAAACCGAG
GCAGCTGACTTCTCAAGGAACTGCATCTGCTTCTCGTCCGCAATGCAAAGCAAGGAATCAGTACATACTTC
TAAAGCCGATGGTGGCGGGGTTGGCTTGAAGTCCTGAAGCTTTGAGTATTCTGTGATGAGGTGAAACATG
TAAGAATAGACTGTATCCATGCTCAAGYTCTCCATGAATT SEQ ID No. 3 - (A) SNP on position 85
TTAAAAAAATAACTTTTATGAAAGTAGCAAAACAAAGAAAMGTTGGAGAAAGTAGTGCTTGCAAGTTTCA
CTCTCGTTTGGTCTGGATTGTTGATACATCTTGGCACATTTTTATGCATGGAAAAAAACTTGAGAATACATT
ATCCTGCAG SEQ ID No. 4 - (A) SNP on position 45
TTAAGAACCACAACACAGTAGCCCCTGGACGCACAAAAGAAAAATACAACAGAAGTTGATGCAGAGGAAC
ATCTACCTGTCCCTGCAGGTCTCAGT SEQ ID No. 5 - (A) SNP on position 26
TTAATGAATCCAAACAGACTGGAAAAATGATTATGTTCCCTGTTACTTTTTCTACAGATTCAGATGGGGTTG
TACCATTATGGGATGCGATACTTGGTGGCCATGAGGCAGTAGCTCAGCTACTTATAGACAATGGTGCTAAC
CTTCGGTCAGGAGATGTCGGCCACTTTGCGTGTACTGCTGCAG SEQ ID No. 6 - (A) SNP on position 41
TCTTGATCCCAACTCAAAGGTCCTGATGCATGCAATGCCTGAATAGTGCAACGGTAGGCTTGTAACTCTAA
CCTATGGAT SEQ ID No. 7 - (A) SNP on position 39
GCGTCCATGCGAACTCGGTCACAGAGCATCTCCTTCTGATGATAGAGAAAGGCGTAAGTGCAGAAATACTG
AGCA SEQ ID No. 8 - (A) SNP on position 91
TTAAGAGTCAGTTTGGTGATAGAAAGAAGATCCATTGGAGGAGCTAGAGAATGATGTGTATGGGCATAGA
CCTTGGTGGGATGGGTTTTCGTGGTTTGGCTTCCGTTGGTCAATCAATGTTGGGGTCTCCTTTTATGGACTC
CAAATAGCCTTCTTGGTGTAAGTCGTTATGGGTACAAACACAAGTCCCCAAAGGAGGCATCTGTGGCATCC
TTGGTGTCACTCTTGGAGAGGATTGGGTAATAGAAAAG SEQ ID No. 9 - (A) SNP on position 84
CTGCAGGCATCTAAGGGAGTGGTGAGCGACAAGATGTTAGCTATTACTCCTTCCGGCAGAGAGGAGAAAT
GGGTTCTTCCTTCTTTACCCTCCATGCTTTTTTTTGGTGTCAAGGGATAGTTTTATTTATTTATTTTAA

Fig. 1B

SEQ ID No. 10 - (A) SNP on position 77
TTAACCCGGGCAAACACCTGGCCACCTTGAACATATGCTCGAGGCAACTGAAAGGTGCAAAAGGTGAGCG
TTTATTGGAGGTGCTCGTCTTGGGTACTTGCAAGGCACAAAGACCTCACCTCGCCTCTCGCTTTAGGCGAGT
GCCCGGCTGCGCCTCAACGACGCTGCAG

SEQ ID No. 11 - (A) SNP on position 187
TTAACGGTGTCAGAACCAAGAATAGAGGATTTTGAGCCATCTGTCAAGGTGACAAATGGGAAAAAGGCGG
GGGACAATGGTGTAAAAAATAAGCTAGAATTACCTGTCATGTGAATTGTGGTACCAAAGTCTATGACCCAT
TTGGTAGATGATGTAAGGAGACACTTTGTATTACCTATGTCAGCGGTGGAGGCGATAGGATTAGAGGAAG
ATGACACTTGCAATGAATCTTGGTACATCTGAAATTTAGC

SEQ ID No. 12 – (A) SNP on position 106
TTAAGAAAATTGGAAAGAGATCAAAATCAGCTGAGTTCTAAAAGATAGTATTTTCGGTGAACCTGGGAGTT
AGAGGATATTTTATATAAGCCCTTATACTTGATAATGGAAGTTGAAATGGACCTTCAACAAAAGTTGGGTT
GAGGTTCCCATCATACTCAAACTTGCTAAACAGGAGCTGCACATGATTATGAAGTGCATGTGAAAAACACC
ATGCAAGGGAGAAAATGAGAAGAAACTAAAAGAAAAGC

SEQ ID No. 13 - (A) SNP on position 40
TGCTTTTTCCAGGTGCATTGCCCATTCAGTTTTCACTGATGAAGTACAGTCTTGCATGGTGGACATTTTCCT
GCTGCAG

SEQ ID No. 14 - (A) SNP on position 62
CTGCAGGGGTTGCAACAGCTCCTCCTGTAATTGCGTCGATAACAACTTTGTCTCGGTTGTTGTTGCTCGCAG
CTGATACTAGAGCTCCCGTCAAAGCACCTCCAATCATTGCATTTTTCTGGAAACAAATGTTCGAATATATGG
AAAATATTCCCAAACAAACATAGAGAGCTGGAAGCACTAATCTAACAGAATAGCTTGAACTTGATTTAA

SEQ ID No. 15 - (A) SNP on position 152
TTAATACAATCCCTATGAAAAAAATGGCCACAATTCTCAATTACTCCACAAATCTCCTCTTCCCCAAATCCCT
CAATACATATCGCACACTTCCTCCCATCGCAATCCCCAATTTCCCCTGTTTTTATTTCTCTAAAACCCATCTTC
ACGGCTGCCGGAATTTCCTCCGACGTCTCCTCCGCTGCAG

Fig. 2A

SEQ ID No. 16 - (A) polymorphism SNP on position 184
GAAGACACAAGAGCTGATATTATCCAATATCTCTGTGGAAGAAATTATTGTAATAGATTGGAGAGGCAATG
GCCAGACTCATAATTACCTGCAACATTTGGAGATTCTTTCAAGTTGGGGTCTTCATTTGCTTCTTGTTTAACC
CATTCATTTCTTCGACTGGAGGTTTCTCATCTGTCTTTAAATTTGTTATAGATTTGGACATAGTTTGTTTTCT
CTCATCTTTGTATTTCTACTTCTCTAGACTTTACCTAGTTACGGAGCTTTCCATAGAGATGCATCTTTACCTA

SEQ ID No. 17 - (B) polymorphism SNP on position 23
TTAAATCAAACCCATTATCAGGGACAACACCACCTTCCAATAAAGAACTTCTAAAAGCAGATTGCCAAGCA
TTCAAAATTGGTTGAGATACAACAGTTTCTTCAACCCATTCATAAGCCTTCTCAACCAATTCCATGTCCCAA
TCAACACCTGCACTTGCAAAAAACTCTTTATGTCCCCTCGAATAGAACCCGGCATTGACCATGCTTCCTCCG
CCAAGGACTCGTCCTCGTATGTTCTCTACGCCATCC

SEQ ID NO. 18 - (A) SNP on position 38
AAACGACAAAGTGTGTGGCTTTTGCCTCCGCGCCTGATATTCTCATTGAATTAGAATTTGGGGTGTTTCCGT
TCGTTG

SEQ ID No. 19 - (B) SNP on position 50
CTGCAGCAGCGAAGGTCGAGCAAATGTGTAAAGRAGTCGAGCGACAACAAAGCTTATCTTCGGATTTCAA
TGTCGAAAGTGGTGAACTC

SEQ ID No. 20 - (A) SNP on position 39
TCAGGATGATAATAATAATCTCCCCAAAGACGGGTAGCGAACTTATCAGCATCAAAAGGGATTCCATGAAG
TTTG

SEQ ID No. 21 - (A) SNP on position 39
GTATGCTTTTTTGTGTGCTCTTTGGATTGTATTCCCTGAATCTCCACTTAGCTCGATGCAAAATTTTCTTCTT
GTT

SEQ ID No. 22 - (A) SNP on position 60
TTTAATCAAAATGATGCATATAGGAAGAATGCATCATACACATTGCCAATGGAACTCTTAGGATATTCAAA
ATGATAGATAGCTAAATGTGGCTTTGGCTTGGATTGAAAAGCAGCAGTTTTGAAACAGACATCTGTTGTTC
ATGAAGTGTTATTGTTTTGTTGAATGTTGTCTCTATCAGCTCCAAATTGATTCTTTTTTCGTTATATGCATTA
GTGTGGTCGGAGATACATGTGTTGCAATGGAAGATT

SEQ ID No. 23 - (A) SNP on position 40
CAGCAGATACCATACCTGCTCCTTCGCACTTATTCCAACAACATCCATAGCTCTTCTAGTGGCAAGATAGTC
ATGAGCAT

SEQ ID No. 24 - (A) SNP on position 171
GATCGGATTATATTTGAAAGAAATAATATNTACTTACCAAGAGAAAATTTGAACATGTTCTCCAAAGCTTG
AAGAAGGTCAGGATATCCTTGATAGATCTTAAGATCAACTTTCCTAAGAAATGGAGCTCCATCCATGCTCA
CTTTTATGAACATTCCGGCCGCCGTCTCCTCTTTTTTCTTTGCTTGTAAAGAATTCTTTCGAAATGATCTCAC
CGGTGGCCACCCCACAACTTGTGCCCTATTAAATATAAAATATTTCTGTCAAATTCTAATTTAAGAAGAAAA
AAAACCCCAAA

Fig. 2B

SEQ ID No. 25 - (A) SNP on position 111
TTGCCTGAAAAAACATTCAAAGAAAGAAAACATCAATAANTTTTCATCATTAAAGAGAGAGATCTCAAGAT
CTAATTAAGAGATCGGATTATATTTGAAAGAAATAATATGTACTTACCAAGAGAAAATTTGAACATGTTCT
CCAAAGCTTGAAGAAGGTCAGGATATCCTTGATAGATCTTAAGATCAACTTTCCTAAGAAANGGAGCTCCA
TCCATGCTCACTTTTATGAACATTCCGGCCGCCGTCTCNTCTTTTTCTTTGCTTGTAAAGAATTCTTTCGAAA
TGATCTCACCGGTGGCCACCCCACAACTTGTGCCCTATTAAATATAAAATATTTCTGTCAAATTCTAATTTA
AGAAGAAAAAAAACCCCAAAATCTAACTAATTTCTAAANTTTTAGAAATAATAAACCAAAACTTTACTGTTT
GATAAAAGTTCTTACTTGGTAGGA

SEQ ID No. 26 - (B) SNP on position 72
ATGTGTCTTCANTGATGGTACTGTTTTGATTCCCATAAACATTTGGGTCAAGCTTACTTGTTGGTGGAAAAA
CCTATATATAATTAATATAAATTGAGATTAATTAGAATCTTTTGGTAAAAAAAATCATTTGAGAAAATTGAG
ACTAATTATTTGTTAAAATCATTACTTCAAGACGACGAATCAATAGAGGATTGGGTCCTGCTAACATTTCTC
TTGCAAATTCTTCATCAGTGCTCCATCCTATTTTATTATCTGTTCAAAATTAATTGTAAATTAATTAAGTATG
ATCAACAAAATTGTATAAACAATTAATGTTAGTATATTCATTCCTCATAATATCTAAATTTTTGTACCTTTGA
CAACTTCGGGAGTAGGAAATTTGAGGAATTTTTCACCATCATTCCTCACGAGTGCTTTGAACAAAGGTGGA
GTGAGGTCCTCAGTGAGGGTCTTAAAAGCATTAAATGGAATGGGAAAACCTCTCAAAGAGATTATCAAC
TTCTTTAAAATTGTCAAATTCATTTGGAGTTACATCAAATATGGATTGAAGTCCTGGTTTGATTGATATCGA
AAGTGCTTTTAATGTATAACCAAGGAAATCTGACATCTTCAAATGCCCAAAGTTTTCATCTTTTGGTACATA
GATGTCTAAGCTCATTATTGGTGACAATCTGCTCTCA

SEQ ID No. 27 - (A) SNP on position 135
TTAATGATGCTATCTTCCGTTTTTCCTTAGATCTTGAAGAGCGTATACTAAAGCAGCAACAAGAAGAAGAA
CAACGAAARCGCGAGCGTCGAGAAGGAAGAAAGAAAAGAAGGTTAGTACTATAATAACCTCATGATTTT
GGCAACAATTTCTATCATGAAAAGWGGGGATCACATCTTACACTTGTGTTTATTCTCCTGGAATGTAGAAA
GAGAAGGCTGCAG

SEQ ID No. 28 - (B) SNP on position 60
TTAATACTTTCTTGCTTTCACTTGTTCTCGATTCAGAATTAGAAGACTCTSCCTCCGATATCCAATTCTATAC
ACAGCATCTAATCCGGGAGCTCGGACGTGAAACGTACATCGGGCAACGTGCAATAGTTTCTGTGTCTCAAA
GAATTGCTGCAG

Fig. 3

Fig. 4
| Line | ratio pericarp vs total surface area |
|------|--------------------------------------|
| 1316 | 0,24 |
| 1317 | 0,22 |
| 1319 | 0,22 |
| Valle | 0,29 |
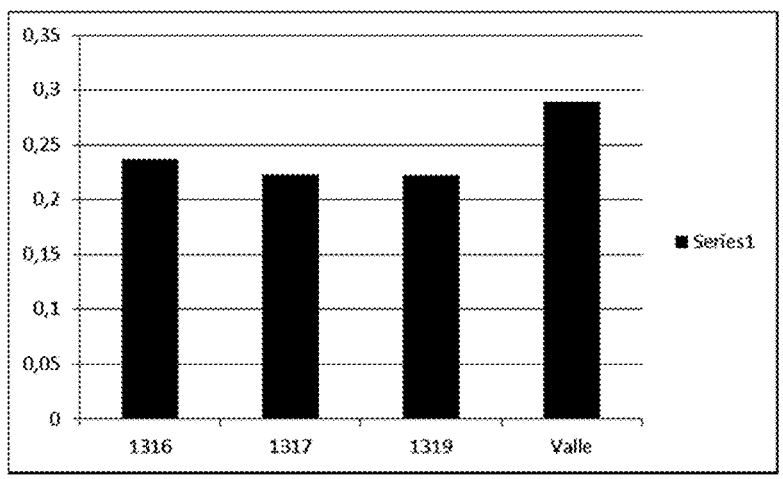
| Line | ratio pericarp vs total surface area |
|------|--------------------------------------|
| 1316 | 0,27 |
| 1317 | 0,23 |
| 1319 | 0,21 |
| Valle | 0,30 |
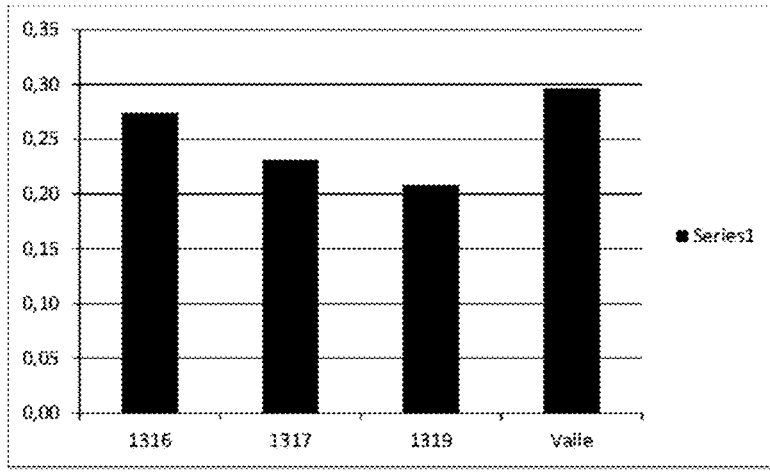

GENETIC BASIS FOR CUCUMBER FRUIT HAVING SMALL SEED CAVITY

RELATED APPLICATIONS AND INCORPORATION BY REFERENCE

This application is a Continuation-in-part Application of International Patent Application Serial No. PCT/EP2016/064831 filed Jun. 27, 2016, which published as PCT Publication No. WO 2016/207432 on Dec. 29, 2016, which claims benefit of European patent application Serial No. 15174148.5 filed Jun. 26, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Oct. 30, 2017, is named 43104002341_SL.txt and is 13,555 bytes in size.

FIELD OF THE INVENTION

The present invention relates to a parthenocarpic cucumber fruit (*Cucumis sativus* L.) which may comprise a genetic determinant that leads to a lower total moisture content, and to a plant producing such fruit. The invention further relates to markers linked to the genetic determinant and the use of markers to identify the genetic determinant. The invention also relates to the seeds and progeny of such plants and to propagation material for obtaining such plants.

BACKGROUND OF THE INVENTION

The food processing industry is a fast growing business which is expected to increase at a steady pace in the years to come. The active and busy lifestyles of consumers, combined with an increasing consciousness for healthy products, results in a growing demand for convenient, fresh and healthy food. The market for fresh-cut vegetables and fruits has grown dramatically as a result of these consumers requirements, and new products are developed continuously to satisfy the desire for creative new products in the convenience market.

Fresh-cut vegetable products include a rather broad range of vegetables such as various types of lettuce, rocket, spinach, corn salad, other leafy vegetables, peppers, carrots, cabbage, celery, and various sprouts. They can be offered individually, or ready-to-use mixes of vegetables can be prepared. Also combinations with fruits, herbs, or nuts, optionally even including seasoning to reach a yet higher level of convenience, are highly attractive to consumers as a basis for a quick and healthy meal or snack.

However, not all vegetables and fruits are considered suitable to be combined into such pre-cut products. Wounding of the plant and fruit tissue due to the cutting or further processing of the vegetables or fruits leads to faster deterioration, which means these products have a limited shelf life. Deterioration can show as discolouration or flaccidity, but also an increased susceptibility to microbial spoilage. Especially vegetables and fruits that contain a high moisture content are often not considered to be eligible for pre-cutting and incorporation into fresh-cut salads or other products.

Cucumber is an example of one of those vegetables that is very difficult to use in the pre-cut convenience market. Even when parthenocarpic cucumber fruits are used, the core or seed cavity is so moist that cutting it leads to too fast spoilage of the resulting product. Still, cucumber is highly desired to be combined into various mixes, since its taste and texture properties can be easily matched with many other products. One solution for this, which is practiced, is that after cutting the core or seed cavity is removed, so that only the drier flesh surrounding it is left to combine into fresh-cut products. This however requires additional costs and labour, and moreover leads to more waste. The potential waste for this process is calculated to reach about 25%.

Another application for which cucumber is less suitable because of its high moisture content is the use in cooking, for example in stir-frying.

It is an object of the present invention to provide a parthenocarpic cucumber fruit that has a lower total moisture content which makes it more suitable to be used in the fresh-cut vegetable industry.

During the research that led to the present invention a genetic determinant, in particular a QTL, was identified that, when present in a parthenocarpic cucumber fruit, results in a small seed cavity of the fruit. The result of the smaller seed cavity is that the contribution of the moisture in the core or seed cavity to the total moisture content of the cucumber fruit is less resulting in a lower total moisture content of the fruit.

Citation or identification of any document in this application is not an admission that such document is available as prior art to the present invention.

SUMMARY OF THE INVENTION

The invention thus relates to a parthenocarpic cucumber fruit which carries a QTL that leads to a small seed cavity.

In one embodiment the invention relates to a parthenocarpic cucumber fruit which carries a QTL1 that leads to a small seed cavity, which QTL1 is located on chromosome 1 between marker sequences SEQ ID No. 1 and SEQ ID No. 2.

In one embodiment the presence of QTL1 that leads to small seed cavity in a parthenocarpic cucumber fruit can be identified by any of the markers on chromosome 1 having SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, and/or SEQ ID No. 15, or any combination of these SEQ ID Nos.

In a preferred embodiment the QTL1 is located on chromosome 1 between marker sequences SEQ ID No. 9 and SEQ ID No. 2. In said preferred embodiment the presence of QTL1 that leads to small seed cavity in a parthenocarpic cucumber fruit can be identified by any of the markers on chromosome 1 having SEQ ID No. 10, SEQ ID No. 11, SEQ ID No. 12, SEQ ID No. 13, SEQ ID No. 14, and/or SEQ ID No. 15, or any combination of these SEQ ID Nos.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

Seeds of cucumber *Cucumis sativus* EX5.006 that comprise QTL1 and QTL2 in heterozygous form and have the phenotypic trait of the invention were deposited with NCIMB Ltd, Ferguson Building, Craibstone Estate, Bucksburn, Aberdeen AB21 9YA, UK on May 21, 2015 under deposit accession number NCIMB 42411.

Seeds of cucumber *Cucumis sativus* EX5.007 that comprise the QTL1 in homozygous form and QTL2 in heterozygous form and have the phenotypic trait of the invention were deposited with NCIMB Ltd, Ferguson Building, Craibstone Estate, Bucksburn, Aberdeen AB21 9YA, UK on Jun. 25, 2015 under deposit accession number NCIMB 42424.

Seeds of cucumber *Cucumis sativus* EX5.011 that comprise QTL1 and QTL2 in homozygous form, and have the phenotypic trait of the invention, were deposited with NCIMB Ltd, Ferguson Building, Craibstone Estate, Bucksburn, Aberdeen AB21 9YA, UK on Jun. 13, 2016 under deposit accession number NCIMB 42590.

The Deposits with NCIMB Ltd, under deposit accession numbers 42411, 42424 and 42590 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A-B: SNP marker sequences of SEQ ID Nos. 1-15 related to QTL1, chromosome 1. Behind the SEQ ID No. it is indicated if version A or B of the sequence is given. The version given is the version that is related to the QTL of the invention (see also FIG. 3). Also the position of the SNP is mentioned, and the nucleotide at that position is bold. Using FIG. 3, the haplotypes for standard cucumber/control plants as compared to the QTL region of plants of the invention can be determined.

FIG. 2A-B: SNP marker sequences of SEQ ID Nos. 16-28 related to QTL2, chromosome 2. See explanation at FIG. 1 for further description.

FIG. 3: Haplotypes of the SNP markers for QTL1 and QTL2. The nucleotide change is indicated as [X/Y], whereby X is version A and Y is version B.

FIG. 4: Comparison surface area cavity sizes

DETAILED DESCRIPTION OF THE INVENTION

Figure 7:
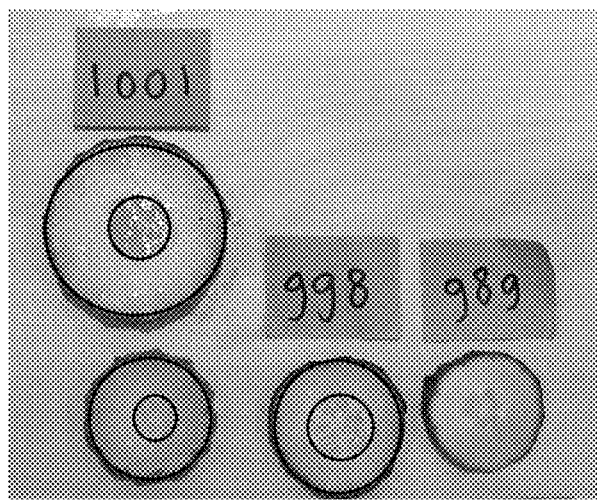
FIG. 7: Cross-section of a cucumber fruit. Within the inner circle is the seed cavity, between the inner circle and the outer circle is the flesh. The slices of number 1001 and the slice of number 989 are from fruits of the invention. The slice of number 998 is from a standard cucumber variety.

The research that led to the present invention focused on the identification of a genetic determinant for creating parthenocarpic cucumber fruits that have a small seed cavity. A 'seed cavity' as used herein is the central area of a cucumber fruit, also called the endocarp, in which the seeds develop or, in case of a parthenocarpic fruit, the area in which the seeds would develop if the flower would have been pollinated and seeds would have developed. Between the seed cavity and the peel of the fruit the flesh, or mesocarp, of the fruit is found (FIG. 7). A small cavity would lead to cucumber parts or slices having less liquid, which cucumber slices are less juicy and therefore have less leakage, which is highly favourable for the cutting industry and for use in cooking.

During the execution of the breeding activities with this goal in mind, it was highly surprisingly found that a combination of cucumber genotypes with fruits showing a regular sized seed cavity could be used to identify a genetic determinant leading to the expression of a small seed cavity when present in parthenocarpic fruits. In this process cucumber plants that had fruits with seeds, and had no capability to produce parthenocarpic fruits, were combined with cucumber plants that were able to develop parthenocarpic fruits. Both types showed a regular seed cavity, i.e. a seed cavity that did not show a remarkable reduction as compared to known cucumber fruits. After continuous breeding, a segregating population was obtained from which a number of plants were capable of parthenocarpic fruit set. In some of these plants it was identified that the fruits that were allowed to develop parthenocarpic showed a remarkably small seed cavity when compared to the seed cavity of the fruits of both parents. Since the expression of this genetic determinant was only visible in a parthenocarpic background, it did not express itself in the fruits that were used as source. The original cucumber plants were not capable of parthenocarpic fruit set, and therefore also not of bearing fruits having a small seed cavity.

A QTL mapping study was performed to identify the genetic region for the cause of this trait. In this study a QTL, designated QTL1, was identified on chromosome 1, between the positions that can be identified with marker sequences SEQ ID No. 1 and SEQ ID No. 2. Further genotyping resulted in the mapping of various SNP markers that can be used for identification of QTL1, which SNP markers are represented by SEQ ID Nos. 3-15 (Example 2). The sequences of SEQ ID Nos. 1-15 related to QTL1 can be found in FIG. 1.

Subsequent fine-mapping on F3 recombinants of backcrossed material further reduced the QTL region of QTL1. The smaller region is flanked by SEQ ID No. 9 and SEQ ID No. 2, and SNP markers for identification within this region are represented by SEQ ID Nos. 10-15.

In the QTL mapping study also a second QTL was identified, designated QTL2. This QTL is located on chromosome 2, between marker sequences SEQ ID No. 16 and SEQ ID No. 17.

In one embodiment the invention relates to a parthenocarpic cucumber fruit which carries a QTL2 that leads to a small seed cavity, which QTL2 is positioned on chromosome 2 between marker sequences SEQ ID No. 16 and SEQ ID No. 17.

Further genotyping of QTL2 led to the mapping of various SNP markers that can be used for the identification of QTL2, which SNP markers are represented by SEQ ID Nos. 18-28 (Example 2). The sequences of SEQ ID Nos. 16-28 related to QTL2 can be found in FIG. 2.

In one embodiment the presence of QTL2 that leads to small seed cavity in a parthenocarpic cucumber fruit can be identified by any of the markers on chromosome 2 having SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, and/or SEQ ID No. 28, or any combination of these SEQ ID Nos.

In one embodiment, the invention relates to a parthenocarpic cucumber fruit which may comprise a QTL1 that leads to a small seed cavity in a parthenocarpic fruit, which QTL1 may be as comprised in a cucumber plant representative seed of which was deposited with the NCIMB under deposit numbers NCIMB 42411 and NCIMB 42424 and NCIMB 42590. Such a fruit of the invention therefore has the same QTL1 as the QTL1 that is present in deposit NCIMB 42411 and/or in deposit NCIMB 42424 and/or in deposit NCIMB 42590.

In one embodiment, the QTL1 that leads to small seed cavity in a parthenocarpic cucumber fruit is introgressed from a cucumber plant which may comprise said QTL1, representative seed of which was deposited with the NCIMB under deposit numbers NCIMB 42411 and NCIMB 42424 and NCIMB 42590.

In one embodiment, the QTL1 may be as comprised in NCIMB 42411 and/or NCIMB 42424 and/or NCIMB 42590 is located on chromosome 1 between marker sequences SEQ ID No. 1 and SEQ ID No. 2, preferably between marker sequences SEQ ID No. 9 and SEQ ID No. 2.

In one embodiment, QTL1 may be as comprised in NCIMB 42411 and/or NCIMB 42424 and/or NCIMB 42590 is linked to any of the markers SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, and/or SEQ ID No. 15, or any combination of these SEQ ID Nos. QTL1 may be as comprised in said deposits is preferably linked to any of the markers having SEQ ID No. 10, SEQ ID No. 11, SEQ ID No. 12, SEQ ID No. 13, SEQ ID No. 14, and/or SEQ ID No. 15, or any combination of these SEQ ID Nos.

In one embodiment, the invention relates to a parthenocarpic cucumber fruit which may comprise a QTL2 that leads to small seed cavity in a parthenocarpic cucumber fruit, which QTL2 may be as comprised in a cucumber plant representative seed of which was deposited with the NCIMB under deposit numbers NCIMB 42411 and NCIMB 42424 and NCIMB 42590. Such a fruit of the invention therefore has the same QTL2 as the QTL2 that is present in deposit NCIMB 42411 and/or NCIMB 42424 and/or NCIMB 42590.

In one embodiment the QTL2 that leads to small seed cavity in a parthenocarpic cucumber fruit is introgressed from a cucumber plant which may comprise said QTL2, representative seed of which was deposited with the NCIMB under deposit numbers NCIMB 42411 and NCIMB 42424 and NCIMB 42590.

In one embodiment the QTL2 which may be as comprised in NCIMB 42411 and/or NCIMB 42424 and/or NCIMB 42590 is located on chromosome 2 between marker sequences SEQ ID No. 16 and SEQ ID No. 17.

In one embodiment the QTL2 which may be as comprised in NCIMB 42411 and/or NCIMB 42424 and/or NCIMB 42590 is linked to any of the markers on chromosome 2 having SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, and/or SEQ ID No. 28, or any combination of these SEQ ID Nos.

In deposit NCIMB 42411 and/or NCIMB 42424 and/or NCIMB 42590 QTL1 is linked to at least one of the markers having SEQ ID No. 3 or SEQ ID No. 4 or SEQ ID No. 5 or SEQ ID No. 6 or SEQ ID No. 7 or SEQ ID No. 8 or SEQ ID No. 9 or SEQ ID No. 10 or SEQ ID No. 11 or SEQ ID No. 12 or SEQ ID No. 13 or SEQ ID No. 14 or SEQ ID No. 15, or to a combination thereof. In deposit NCIMB 42411 and/or NCIMB 42424 and/or NCIMB 42590 QTL1 is preferably linked to at least one of the markers having SEQ ID No. 10 or SEQ ID No. 11 or SEQ ID No. 12 or SEQ ID No. 13 or SEQ ID No. 14 or SEQ ID No. 15, or to a combination thereof.

In deposit NCIMB 42411 and/or NCIMB 42424 and/or NCIMB 42590 QTL2 is linked to at least one of the markers having SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, and/or SEQ ID No. 28, or to a combination thereof.

The terms "small seed cavity" or "smaller seed cavity" of a parthenocarpic fruit as used herein is intended to refer to a seed cavity that is smaller than the seed cavity of a parthenocarpic control fruit of a control cucumber plant, in particular a plant of a standard cucumber variety. The term "standard variety" as used herein is intended to refer to any of the cucumber varieties that are currently grown for parthenocarpic cucumber production. The skilled person in the field of cucumber breeding and growth is well aware which varieties are to be considered as standard varieties.

In particular, the cucumber fruit of a control cucumber plant, i.e. a cucumber plant having a similar or same genetic background but not comprising QTL1 and/or QTL2 as defined herein, can be used as a comparison for seed cavity size. A plant having a similar genetic background is for example a cucumber plant that belongs to the same type of cucumbers, for example both belong to a long cucumber type, also known as a European greenhouse cucumber type, or both belong to a slicer type, or to a Beit-Alpha type, or to a pickling type. A plant having the same genetic background is also called an isogenic plant, which is genetically the same as the plant of the invention to be assessed, but lacks the QTL1 and/or the QTL2 of the invention and therefore does not have the small seed cavity of the invention in a parthenocarpic fruit.

A small or a smaller seed cavity of a parthenocarpic fruit of the invention as used herein is a seed cavity of which the ratio of the surface area of the seed cavity in relation to the total surface area of a fruit cut in cross-section in $cm^2$ in order of increased preference is at least 5% smaller, 10% smaller, 15% smaller, 20% smaller, 23% smaller, 24% smaller when compared to the ratio of the seed cavity of a parthenocarpic fruit of a control plant in relation to its total surface area of a fruit cut in cross-section in $cm^2$ (Example 1). The cross-section is to be made at a location sufficiently far removed from the ends of the cucumber for a cavity to be present. The cross-section is in particular made around the middle of the cucumber.

In one embodiment the surface areas that are used for comparing the size of the seed cavity are calculated by using the method as described in Example 1.

Alternatively a small or a smaller seed cavity of a parthenocarpic fruit of the invention can be calculated as the ratio of the diameter of the seed cavity and the total diameter of a cross-section of a parthenocarpic fruit. In a parthenocarpic fruit of the invention this ratio in order of increased preference is at least 5% smaller, 7% smaller, 10% smaller, 12% smaller, 15% smaller when compared to the ratio of a parthenocarpic fruit of a control plant.

The skilled person is aware that to determine a significant difference a suitable trial set-up has to be established, whereby an appropriately large number of fruits of a reasonable number of plants per line or genotype is assessed, wherein the fruits are preferably grown under optimum growing conditions. The lines to be compared should be uniform. A suitable trial set-up would for example may comprise at least five fruits per genotype, which are harvested at least twice with an interval of for example one month. Assessment should start when plants are in production, for example at 4 weeks after planting. Recommended growing conditions are in a greenhouse, most optimal is a greenhouse with high-wire facilities, to ensure that fruits can develop uniformly and to their best potential. Fruit assessment should preferably be done on fruits from the main stem, and should be performed on fruits at their harvestable stage, meaning the stage they are harvested for commercial purposes. Comparison of seed cavities can only be done between fruits that are grown in the same trial, i.e. in the same location under the same environmental conditions.

In a preferred embodiment a parthenocarpic cucumber fruit of the invention is a cucumber fruit of a so-called long cucumber type, also known as a European greenhouse cucumber type.

Figure 5:
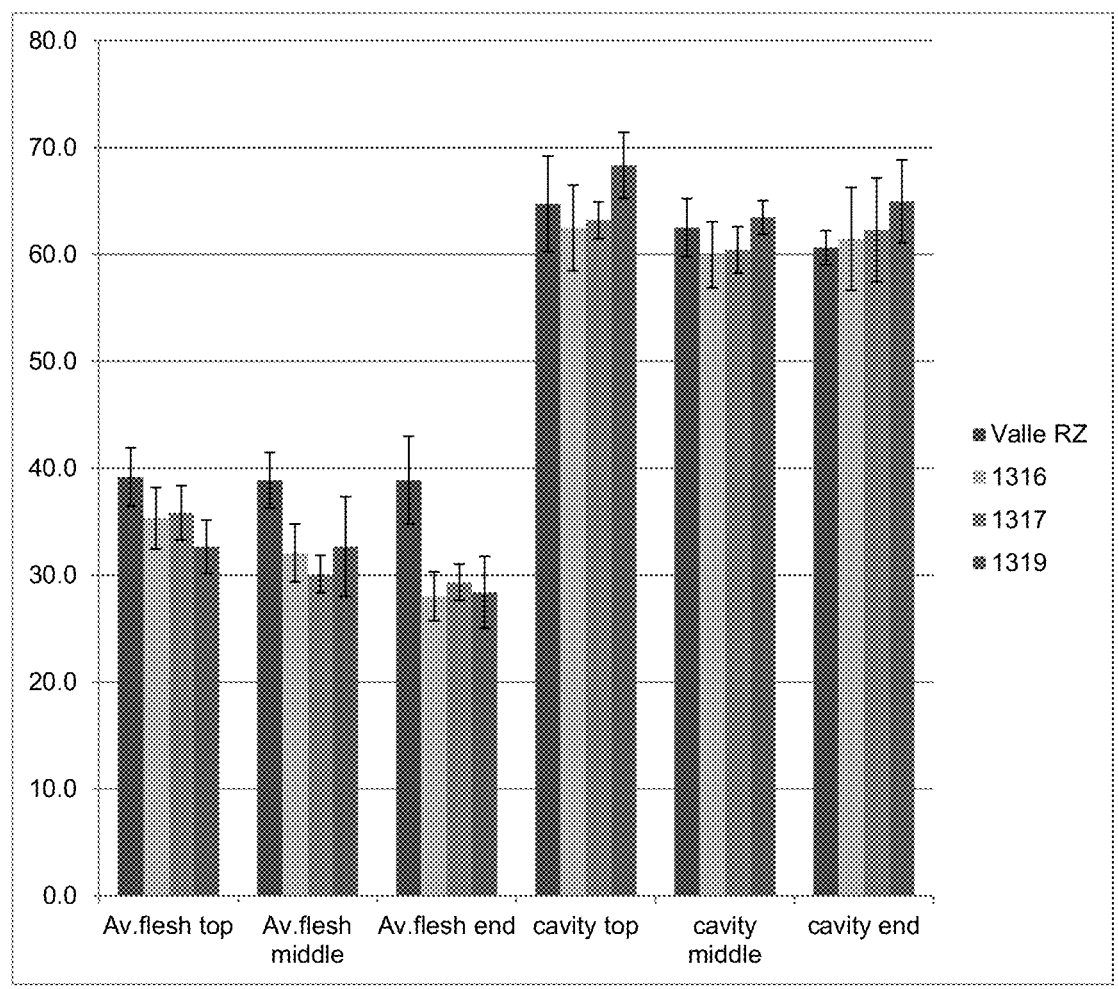
FIG. 5: Comparison moisture content

Further research on the parthenocarpic cucumber fruits having a small seed cavity confirmed that in general the flesh of a parthenocarpic cucumber fruit, or of a slice or part of the fruit, is drier than the cavity of a slice or part of such fruit (Example 3, FIG. 5). Since in a fruit of the invention the share of the flesh is relatively larger than the share of the cavity, and the share of the flesh is larger than the share of the flesh of a fruit of a standard variety, overall the total moisture content of the parthenocarpic fruits of the invention will be lower, and the fruits or parts of a fruit will be drier. Moreover, the slices or parts of cucumber fruits of the invention have less leakage after storage when compared to fruits from control cucumber plants (Example 4, FIG. 6). In addition, it was observed that the flesh of a parthenocarpic fruit of the invention is drier than the flesh of a control parthenocarpic fruit (Example 5, FIG. 5). These results show the high suitability of fruits of the invention for use in the food processing industry, especially for use in the fresh-cut vegetable and fruit convenience market and for use in cooking, for example stir-frying.

Introgression of a QTL as used herein means introduction of a QTL from a donor plant which may comprise said QTL into a recipient plant not carrying said QTL by standard breeding techniques, wherein selection can be done phenotypically by means of observation of the trait of small seed cavity, or selection can be done with the use of markers through marker assisted breeding, or combinations of these. Selection is started in the F 1 or any further generation from a cross between the recipient plant and the donor plant, suitably by using markers as identified herein. The skilled person is however familiar with creating and using new molecular markers that can identify or are linked to the trait of small seed cavity. Development and use of such markers for identification and selection of fruits of the invention is also part of the invention.

In one embodiment a parthenocarpic cucumber fruit of the invention may comprise a combination of QTL1 and QTL2. In one embodiment the invention relates to a parthenocarpic cucumber fruit which may comprise QTL1 and QTL2 as defined herein, the presence of which QTL1 and QTL2 leads to a small seed cavity of the fruit.

In one embodiment a parthenocarpic cucumber fruit of the invention with a small seed cavity may comprise QTL1 and/or QTL2 in homozygous form. In one embodiment a parthenocarpic cucumber fruit of the invention with a small seed cavity may comprise QTL1 in homozygous form and QTL2 in heterozygous form, or may comprise QTL1 in heterozygous form and QTL2 in homozygous form, or may comprise both QTL1 and QTL2 in heterozygous form. When two alleles of at least one of QTL1 and QTL2 are present in a parthenocarpic fruit the small seed cavity is visible. An allele of QTL1 and/or QTL2 as used herein is the version of the QTL that leads to a small seed cavity. The presence of an allele of QTL1 or QTL2 can suitably be identified using any one of the markers as described herein. The presence of at least two alleles means that QTL1 can be present homozygously, or QTL2 can be present homozygously, or both QTLs can be present heterozygously. Optionally one or two additional alleles can be present in a fruit of the invention that has a small seed cavity.

The invention also relates to a cucumber fruit or a cucumber plant carrying only one allele of QTL1 or QTL2, which plant or fruit can be used as a source for the development of a plant or parthenocarpic fruit of the invention which may comprise at least two alleles of at least one of QTL1 and QTL2.

In deposit number NCIMB 42411 QTL1 and QTL2 are both present in heterozygous form. In deposit number NCIMB 42424 QTL1 is present in homozygous form and QTL2 is present in heterozygous form. In deposit number NCIMB 42590 QTL1 and QTL2 are both present in homozygous form.

The invention also relates to a cucumber plant comprising QTL1 and/or QTL2, which plant is capable of producing parthenocarpic fruits that have a small seed cavity. The invention further relates to the use of such plant of the invention for the production of parthenocarpic fruits that have a small seed cavity.

The invention further relates to a method for the production of a parthenocarpic cucumber fruit having a small cavity, which may comprise providing a plant having QTL1 and/or QTL2 as defined herein, growing said plant, and allowing the fruit to develop without pollination. Upon harvest the parthenocarpic cucumber fruit having a small cavity is obtained.

The invention also relates to the use of a plant of the invention that may comprise QTL1 and/or QTL2 as a source of propagating material.

The invention also relates to the use of a plant of the invention that may comprise QTL1 and/or QTL2 in plant breeding.

In one embodiment the invention relates to a part of a parthenocarpic cucumber fruit of the invention which may comprise QTL1 and/or QTL2, particularly to a fruit part that may comprise the small seed cavity of the invention. Optionally the small seed cavity of such part is removed. The remaining part has then a larger flesh surface when compared to fruits from a control plant from which the seed cavity is removed. Parts of a fruit of the invention are optionally in processed form, for example the part is a slice, a part of a slice, a cube, or any other part of a fruit. Processed fruit parts can optionally be mixed with other vegetables, fruits, or other food products, and such mixture which may comprise a fruit or part of a fruit of the invention which may comprise one or both of the QTLs and is therefore also a part of the invention. Processed food products are optionally packaged in a container or bag, and such packaged food product which may comprise a fruit or part of a fruit of the invention is also a part of the invention. The invention also relates to the use of a parthenocarpic fruit of the invention having a small seed cavity for further processing into a processed food product by cutting, slicing, peeling, or any other treatment, optionally followed by mixing with one or more other food products.

The invention furthermore relates to a cell of a plant as claimed. Such cell may be either in isolated form or may be part of the complete plant or parts thereof and then still constitutes a cell of the invention because such a cell harbors the genetic information that leads to a small seed cavity of a parthenocarpic cucumber fruit. Each cell of a plant of the invention carries the genetic information that leads to a small seed cavity of a parthenocarpic cucumber fruit. Such a cell of the invention may also be a regenerable cell that can be used to regenerate a new plant of the invention. The presence of genetic information as used herein is the presence of QTL1 and/or QTL2 as defined herein.

The invention also relates to tissue of a plant as claimed. The tissue can be undifferentiated tissue or already differentiated tissue. Undifferentiated tissues are for example stem tips, anthers, petals, pollen, and can be used in micropropagation to obtain new plantlets that are grown into new plants of the invention. The tissue can also be grown from a cell of the invention.

The invention according to a further aspect thereof relates to seed, wherein the plant that can be grown from the seed is a plant of the invention, which may comprise QTL1 and/or QTL2 which leads to small seed cavity in a parthenocarpic fruit of a plant that is capable of producing parthenocarpic fruits. The invention also relates to seeds of a plant as claimed, which can be obtained after pollination. The seeds harbor the QTL1 and/or QTL2 that, when a plant is grown from the seeds, makes this plant a plant of the invention.

The invention also relates to progeny of the plants, cells, tissues and seeds of the invention, which progeny may comprise QTL1 and/or QTL2 that leads to small seed cavity. Such progeny can in itself be plants, cells, tissues, or seeds.

As used herein the word 'progeny' is intended to mean the first and all further descendants from a cross with a plant of the invention that may comprise QTL1 and/or QTL2 that leads to small seed cavity.

'Progeny' also encompasses plants that carry QTL1 and/or QTL2 of the invention and have the trait of the invention, and are obtained from other plants or progeny of plants of the invention by vegetative propagation or multiplication. Progeny of the invention suitably may comprise QTL1 and/or QTL2 and the trait of the invention.

The term "trait of the invention" as used herein is intended to refer to the trait of having a small seed cavity in a parthenocarpic fruit.

The invention further relates to parts of a claimed plant that are suitable for sexual reproduction. Such parts are for example selected from the group consisting of microspores, pollen, ovaries, ovules, embryo sacs, and egg cells. In addition, the invention relates to parts of a claimed plant that are suitable for vegetative reproduction, which are in particular cuttings, roots, stems, cells, protoplasts. The parts of the plants as mentioned above are considered propagation material. The plant that is produced from the propagation material may comprise QTL1 and/or QTL2 that leads to a parthenocarpic fruit having small seed cavity.

According to a further aspect thereof the invention provides a tissue culture of a plant carrying the QTL1 and/or QTL2 of the invention, which is also propagation material. The tissue culture may comprise regenerable cells. Such tissue culture can be selected or derived from any part of the plant, in particular from leaves, pollen, embryos, cotyledon, hypocotyls, meristematic cells, roots, root tips, anthers, flowers, seeds, and stems. The tissue culture can be regenerated into a plant carrying the QTL1 and/or QTL2 of the invention, which regenerated plant expresses the trait of the invention and is also part of the invention.

The invention furthermore relates to hybrid seed and to a method for producing such hybrid seed which may comprise crossing a first parent plant with a second parent plant and harvesting the resultant hybrid seed, wherein said first parent plant and/or said second parent plant has the QTL1 and/or QTL2 of the invention. The resulting hybrid plant that may comprise the QTL1 and/or QTL2 of the invention and which shows a small seed cavity in the parthenocarpic fruits is also a plant of the invention.

In one embodiment the plant of the invention which may comprise the QTL1 and/or QTL2 of the invention either homozygously or heterozygously is a plant of an inbred line, a hybrid, a doubled haploid, or a plant of a segregating population.

The invention also relates to a method for the production of a cucumber plant having the QTL1 and/or QTL2 that leads to a small seed cavity in parthenocarpic fruits by using a seed that may comprise QTL1 and/or QTL2 for growing the said cucumber plant. The seeds are suitably seeds of which a representative sample was deposited with the NCIMB under deposit numbers 42411 or 42424 or 42590.

In one embodiment, the invention relates to cucumber plants of the invention that carry the QTL1 and/or QTL2 of the invention which leads to a small seed cavity in parthenocarpic fruits, and that have acquired said QTL1 and/or QTL2 from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the QTL1 and/or QTL2 of the invention is acquired is formed by plants grown from seeds of which a representative sample was deposited under accession number NCIMB 42411 or NCIMB 42424 or NCIMB 42590, or from the deposited seeds NCIMB 42411 and/or NCIMB 42424 and/or NCIMB 42590, or from sexual or vegetative descendants thereof, or from another source which may comprise the QTL1 and/or QTL2 as defined herein that leads to the trait of the invention, or from a combination of these sources.

In a preferred embodiment, the invention relates to non-transgenic *Cucumis sativus* plants. The source for acquiring the QTL1 and/or QTL2 of the invention, to obtain a plant of the invention that has a small seed cavity in parthenocarpic fruits, is suitably a *Cucumis sativus* plant that carries the QTL1 as comprised heterozygously in NCIMB 42411 or as comprised homozygously in NCIMB 42424 and NCIMB 42590, or the QTL2 as comprised heterozygously in NCIMB 42411 and/or in NCIMB 42424, or as comprised homozygously in NCIMB 42590, or alternatively a plant of a *Cucumis* species that carries one or both of said QTLs and that can be crossed with *Cucumis sativus*. Optionally, after crossing with a related species, techniques such as embryo rescue, backcrossing, or other techniques known to the skilled person can be performed to obtain seeds of the interspecific cross, which seeds can be used as the source for further development of a non-transgenic *Cucumis sativus* plant that shows a small seed cavity in the parthenocarpic fruits.

To obtain a QTL from a source in which it is heterozygously present, seeds of such plant can be grown and flowers can be pollinated with pollen from the same plant or from a plant that also has the QTL heterozygously to obtain fruits with seeds. When these seeds are sown, the resulting plants will segregate according to normal segregation ratios, which means that about 25% of the plants will have the QTL homozygously, about 50% will have the QTL heterozygously, and about 25% will not have the QTL. The presence of the QTL for selection of a preferred plant, having the QTL either homozygously or heterozygously, can suitably be determined using the markers as described herein. Alternatively, fruits can be phenotypically observed and fruits of plants of the invention can be visually selected for the presence of a small seed cavity, when care is taken that no pollination of the flowers has taken place so parthenocarpic fruits have developed. The skilled person is aware of how to combine QTLs in heterozygous and homozygous form using known breeding and selection procedures.

The invention also relates to the germplasm of plants of the invention. The germplasm is constituted by all inherited characteristics of an organism and according to the invention encompasses at least the trait of the invention. The germplasm can be used in a breeding programme for the development of cucumber plants having a small seed cavity in their parthenocarpic fruits. The use of the germplasm that may comprise the QTL1 and/or QTL2 leading to a small seed cavity in parthenocarpic fruits in breeding is also part of the present invention.

The invention also concerns the use of the QTL1 and/or QTL2 leading to the trait of the invention for the development of cucumber plants that have a small seed cavity in parthenocarpic fruits.

As used herein, a marker is genetically linked to a QTL and can be used for identification of that QTL when the recombination between marker and QTL, i.e. between marker and trait, is less than 5% in a segregating population resulting from a cross between a plant which may comprise the QTL and a plant lacking the QTL.

In one embodiment the invention relates to a marker for identification of QTL1 which leads to a small seed cavity in a parthenocarpic cucumber fruit, which marker is selected from the group of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, and SEQ ID No. 15. In one embodiment the invention relates to a marker for identification of QTL2 which leads to a small seed cavity in a parthenocarpic cucumber fruit, which marker is selected from the group of SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, and SEQ ID No. 28.

In one embodiment, the invention relates to the use of a marker for identification of QTL1 which leads to a small seed cavity in a parthenocarpic cucumber fruit, which marker is selected from the group of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, and SEQ ID No. 15. In one embodiment the invention relates to the use of a marker for identification of QTL2 which leads to a small seed cavity in a parthenocarpic cucumber fruit, which marker is selected from the group of SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, and SEQ ID No. 28.

In one aspect the invention relates to a method for production of a cucumber plant that has a small seed cavity in parthenocarpic fruits, which may comprise the QTL1 and/or QTL2 that leads to a small seed cavity in parthenocarpic fruits, which may comprise:

a) crossing a plant which may comprise the QTL1 and/or QTL2 of the invention, representative seed of which plant was deposited as NCIMB 42411 and/or NCIMB 42424 and/or NCIMB 42590, with a plant not comprising the same QTL, to obtain an F1 population;

b) optionally performing one or more rounds of selfing and/or crossing a plant from the F1 to obtain a further generation population;

c) selecting a plant that may comprise QTL1 and/or QTL2 and has a small seed cavity in parthenocarpic fruits, suitably by using molecular markers linked to one or both of the desired QTLs. The plant can also be phenotypically selected for having a small seed cavity.

The invention additionally provides a method of introducing another desired trait into a cucumber plant which may comprise a small seed cavity in parthenocarpic fruits, which may comprise:

a) crossing a cucumber plant which may comprise the QTL1 and/or QTL2 that leads to a small seed cavity in parthenocarpic fruits, representative seed of which was deposited with the NCIMB as NCIMB 42411 and/or NCIMB 42424 and/or NCIMB 42590, with a second cucumber plant that may comprise the other desired trait to produce F1 progeny;

b) selecting an F1 progeny that may comprise a QTL for the small seed cavity and may comprise the other desired trait;

c) crossing the selected F1 progeny with either parent, to produce backcross progeny;

d) selecting backcross progeny which may comprise a QTL for the small seed cavity and the other desired trait; and e) optionally repeating steps c) and d) one or more times in succession to produce selected fourth or higher backcross progeny that may comprise the other desired trait and has a small seed cavity in parthenocarpic fruits. The invention includes a cucumber plant produced by this method and the cucumber fruit obtained therefrom.

Optionally selfing steps are performed after any of the crossing or backcrossing steps. Selection for a plant which may comprise the QTL1 and/or QTL2 of the invention and the other desired trait can alternatively be done following any crossing or selfing step of the method.

The invention further provides a method for the production of a cucumber plant capable of producing parthenocarpic fruits with a small seed cavity as defined herein by using a doubled haploid generation technique to generate a doubled haploid line that homozygously may comprise the QTL1 and/or QTL2 that leads to the small seed cavity in a parthenocarpic fruit.

The invention also relates to a method for the production of a cucumber plant which may comprise the QTL1 and/or QTL2 that leads to the small seed cavity of the invention, by using a seed that may comprise the QTL1 and/or QTL2 in its genome that leads to the small seed cavity in a parthenocarpic fruit of the invention for growing the said cucumber plant. The seeds are suitably seeds of which a representative sample was deposited with the NCIMB under deposit numbers NCIMB 42411 and NCIMB 42424 and NCIMB 42590.

The invention also relates to a method for seed production which may comprise growing cucumber plants from seeds of the invention, allowing the plants to produce seeds by allowing pollination to occur, and harvesting those seeds. Production of the seeds is suitably done by crossing or selfing. Preferably, the seeds so produced have the capability to grow into plants that produce parthenocarpic fruits having a small seed cavity. To produce parthenocarpic fruits pollination has to be prevented during fruit formation. The presence of a small seed cavity due to the presence of QTL 1 and/or QTL2 in a parthenocarpic fruit showed no negative effect on seed quality or seed quantity of pollinated fruits compared to standard varieties.

In one embodiment, the invention relates to a method for the production of a cucumber plant having the QTL1 and/or QTL2 that leads to a small seed cavity, by using tissue culture of plant material that carries the QTL1 and/or QTL2 in its genome.

The invention furthermore relates to a method for the production of a cucumber plant having the QTL1 and/or QTL2 that leads to a small seed cavity, by using vegetative reproduction of plant material that carries the QTL1 and/or QTL2 in its genome.

Also part of the invention is a method for the production of cucumbers with a small seed cavity, which may comprise growing plants that carry QTL1 and/or QTL2 in their genome, inducing parthenocarpic fruit formation by preventing pollination and harvesting the mature cucumber fruits having a small seed cavity.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Phenotyping of Small Seed Cavity in Parthenocarpic Fruits

Breeding material that had a small seed cavity phenotype in a parthenocarpic fruit was developed by using combinations of various germplasm sources, none of which had the ability to develop parthenocarpic fruits and also no small seed cavity was observed in these sources. However, during the breeding process this remarkable trait was observed, and these fruits were subsequently carefully analyzed.

Visual observation by the breeder leads to a reliable determination of whether a fruit has a small seed cavity or not, and this was how the breeding lines were developed. However, to quantify the small seed cavity, various measurement protocols were developed as well.

In one protocol image analysis was performed to obtain reproducible measurements of the surface area of a slice of a fruit and of the seed cavity of that slice. To perform the image analysis a software program known as 'Tomato analyzer' was used. This program can be downloaded for free, for example from http://www.oardc.ohio-state.edu/vanderknaap/tomato_analyzer.php. A manual on how to use the program can be found at the same website. Although this program was designed for use in analysis of tomato fruits, it is also very suitable for measuring other fruits, such as in this case cucumber slices. Since the seed cavity of a parthenocarpic cucumber fruit often roughly has a triangular shape rather than a circular shape, manual adjustment to indicate the correct boundaries of the seed cavity was performed to obtain accurate measurements.

In one experiment using the Tomato Analyzer program three lines having parthenocarpic fruits with a small seed cavity, identified as 1316, 1317, and 1319, were compared with a control variety Valle F1. Of each line 5 fruits were used, and from each fruit three slices were cut in cross-section at different locations of the fruit (towards the top, at the center, and towards the end). Surface areas of each whole slice in $cm^2$ were measured with aid of the Tomato Analyzer program, and also the surface area of the seed cavity of each slice in $cm^2$. Subsequently the ratio of each seed cavity in relation to the surface area of the slice was calculated from these measurements.

The described experiment was repeated one month later. The average ratios that were calculated can be found in FIG. 4. Both experiments confirmed that the seed cavities of parthenocarpic fruits of 1316, 1317, and 1319 were smaller than the seed cavities of parthenocarpic fruits from the control variety Valle F1.

Example 2

QTL Mapping

A population of plants segregating for the presence of parthenocarpic fruits having a small seed cavity was used for phenotyping and genotyping to determine the genetic background of this trait and for mapping the involved QTLs. To make sure the contribution of all sources was included subsequently BC2F2 generations, BC4F2 generations, and BC5F2 generations of different breeding lines that still segregated for the trait were involved in the mapping. To finalize and confirm the mapping also DH lines that are genetically stable were analyzed.

In a first round 91 SNP markers distributed over the whole cucumber genome were included to get a rough indication of the possible location of QTLs involved in this trait. Regions on chromosome 1 and 2 were identified in this way as potential candidates for the QTL location.

To define the QTL regions better, a follow-up mapping study still included SNP markers on all chromosomes, but focused on chromosome 1 and 2 by including 18 markers for chromosome 1 and 37 for chromosome 2. This resulted in a clearer indication of the QTL regions involved. Following this, an analysis on BC5F2 material confirmed the presence of a QTL on chromosome 1 and a QTL on chromosome 2 to be involved in this particular trait.

Figure 3:
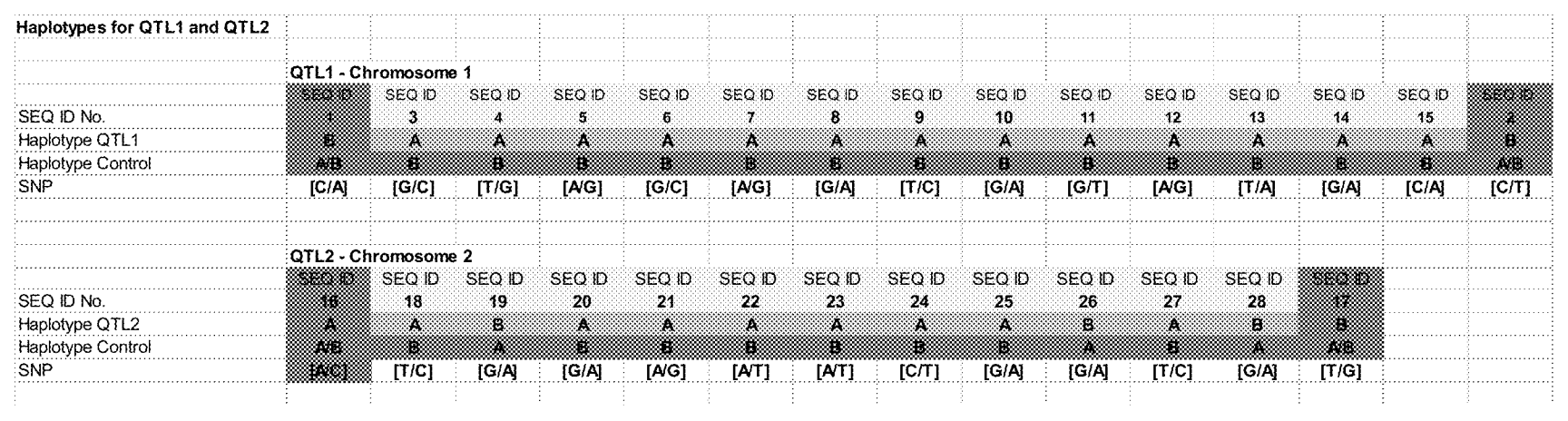

In a final study on DH material, parent lines, and F1's the QTLs were defined to be present between SEQ ID No. 1 and SEQ ID No. 2 on chromosome 1, and between SEQ ID No. 16 and SEQ ID No. 17 on chromosome 2. The SEQ ID Nos. that limit the QTL regions and the SNP markers that are related to the QTL can be found in FIG. 1 for chromosome 1 and in FIG. 2 for chromosome 2. For each SEQ ID No. the version with the SNP that is related to the QTL is presented. The haplotypes that show the order of the SNP markers and the version that is related to the QTL and to the trait are presented in FIG. 3.

Example 3

Moisture Content of Flesh and Seed Cavity of a Parthenocarpic Cucumber Fruit To determine the moisture content of the fruit flesh and the seed cavity of parthenocarpic cucumber fruits measurements were taken from a number of materials. For fruits having a small seed cavity, three hybrids identified as 1316, 1317 and 1319 were used, whereby 1317 is deposited as NCIMB 42424; as a control Valle F1 RZ was used. From each line a minimum of four fruits was measured.

From each fruit that was to be observed a slice of 3 cm thickness was cut towards the top, a slice of 3 cm at the center, and a slice of 3 cm towards the end of the fruit. With an apple corer having a diameter of 9.17 mm, two punches were made from the flesh of each slice, and one punch from the seed cavity. This resulted in three 3 cm long punches from each slice. After this, each punch was lengthwise divided into three equal parts, ending up with six samples of 10 mm long from the flesh of each slice, and three samples of 10 mm long from the seed cavity part of each slice.

To measure the moisture content of these samples, the three samples that resulted from one punch were placed together between two filter papers. For the samples resulting from the seed cavity, wire netting was placed between samples and filter paper to prevent sticking of the samples to the paper. The samples then were crushed between the filter papers by using a texture analyzer that had a 50 kg crushing force. After this the crunched leftovers of the fruit samples were removed.

By determining the weight of the papers before measurements, the weight of papers+samples, and the weight of the filter papers that had taken up the moisture after crushing, the moisture loss of the samples could be determined. From this, the percentage juice that was present in each punch could be calculated. The averages of the results per slice are given in Table 1 and are graphically depicted in FIG. 5.

TABLE 1

| percentage moisture content of fruit flesh and seed cavity | | | | | | | |
|---|---|---|---|---|---|---|---|
| Plot | | Av. flesh top | Av. flesh middle | Av. flesh end | cavity top | cavity middle | cavity end |
| 1316 | average | 35.3 | 32.1 | 28.0 | 62.5 | 60.0 | 61.5 |
| 1317 | average | 35.8 | 30.1 | 29.3 | 63.2 | 60.4 | 62.3 |
| 1319 | average | 32.7 | 32.7 | 28.4 | 68.3 | 63.5 | 65.0 |
| Valle RZ | average | 39.2 | 38.9 | 38.9 | 64.7 | 62.5 | 60.6 |

The results of this experiment clearly indicated that the percentage moisture content of the seed cavity is much higher than the percentage moisture content of the fruit flesh. This confirms that when the seed cavity is much smaller, the total moisture content of a fruit slice, fruit part, or total fruit will be strongly reduced. Surprisingly, the results found also seemed to indicate a trend that the moisture content of flesh of fruits having a small seed cavity and the QTLs that are described in this application, has a lower moisture content on itself, i.e. is drier, than the fruit flesh of a regular parthenocarpic cucumber fruit. This does even enhance the effect of the presence of the small seed cavity, and makes the fruits even more suitable for use in the pre-cut vegetable industry.

Example 4

Leakage Analysis of Cucumber Slices Having Small Seed Cavity

Parthenocarpic cucumber fruits with a small cavity were compared to regular parthenocarpic control cucumber fruits to determine the leakage of fruits that were cut in parts. The fruits having a small seed cavity were of three different F1 test-hybrids, 1316, 1317, deposited as NCIMB 42424, and 1319; as control the variety Valle F1 RZ was used. All hybrids were of the long cucumber type. Of each hybrid four fruits were measured.

After removing the end parts of the fruits, the fruits were cut into slices of about 1 cm thick, whereby from each fruit slices from top, middle, and bottom end were included. The skin was not removed. Each slice was then cut into four parts. The parts coming from the same fruit were placed into plastic boxes of which the weight was taken, and then the weight of the fruit parts including the boxes was taken. Boxes were closed with a lid.

Boxes were then stored in a refrigerator at about 5-6° C. After 7, 14, and 21 days the boxes and fruit parts were taken out and weighed together to determine if there was any general weight loss due to other factors. To determine the leakage, fruit parts were then taken out of the box with a sieve, and the box with the remaining juice was weighed. The weight of the slices and the percentage weight loss due to leakage could subsequently be calculated.

TABLE 2

| | weight loss and leakage | | | | | | |
|---|---|---|---|---|---|---|---|
| | Av. starting weight fruit parts (g.) | Av. weight juice 7 days (g.) | Av. % weight loss slices 7 days (g.) | Av. weight juice 14 days (g.) | Av. % weight loss slices 14 days (g.) | Av. weight juice 21 days (g.) | Av. % weight loss slices 21 days (g.) |
| 1316 | 34.8 | 1.35 | 0.81 | 3.4 | 1.84 | 7.95 | 4.48 |
| 1317 | 34.8 | 1.95 | 0.82 | 3.25 | 1.59 | 7.45 | 3.52 |
| 1319 | 34.9 | 2.08 | 0.82 | 2.7 | 1.22 | 5.7 | 2.61 |
| Valle RZ | 35 | 5.3 | 2.36 | 6.4 | 3.2 | 11.78 | 5.39 |

From this experiment it was very clear that the fruit parts from hybrids that had a small seed cavity had significantly less leakage than the control variety. Especially after 7 and 14 days the control had a lot more juice left in the box than the test varieties, and even after 21 days the difference was significant. This confirmed that the fruits with the small cavity have a great advantage for use in the fresh market processing industry.

Figure 6:
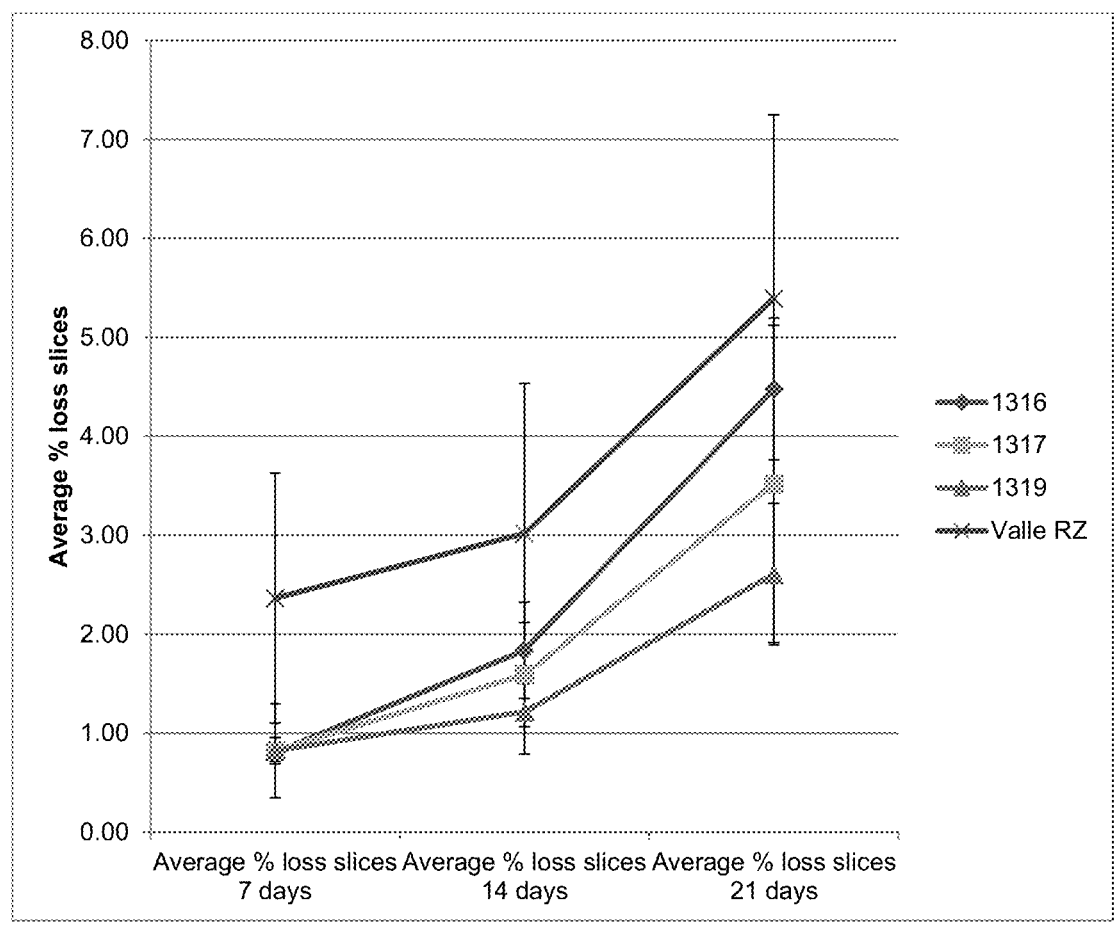
FIG. 6: Comparison leakage

The results are graphically illustrated in FIG. 6.

In a follow-up experiment again parthenocarpic fruits comprising QTL1 and/or QTL2 were compared, whereby 1317, which is NCIMB 42424, and 1319 were included, together with EX5.006 which is deposited as NCIMB 42411. This time the fruits were compared with another commercially available variety, Laureen RZ. This variety has a regular seed cavity and does not have QTL1 or QTL2 of the invention. The set-up was slightly different from the first trial.

At the start of the trial the seed cavity ratios were calculated, of which results are presented in Table 3.

TABLE 3

| Cavity ratios | |
|---|---|
| Number | Cavity ratio |
| 14DL 1317 | 0.30 |
| 14DL 1319 | 0.33 |
| EX5.006 | 0.39 |
| Laureen RZ | 0.46 |

Five plants were sown per number, and of each ten parthenocarpic stem fruits were harvested 5 weeks after planting them in the greenhouse. Each fruit was quartered along the length, and then cut in pieces of 1 cm. These pieces were placed in a plastic net that was prepared to fit in a square plastic box per accession. The boxes were closed, and the combinations were stored in a refrigerator for 4 weeks.

Figure 8:
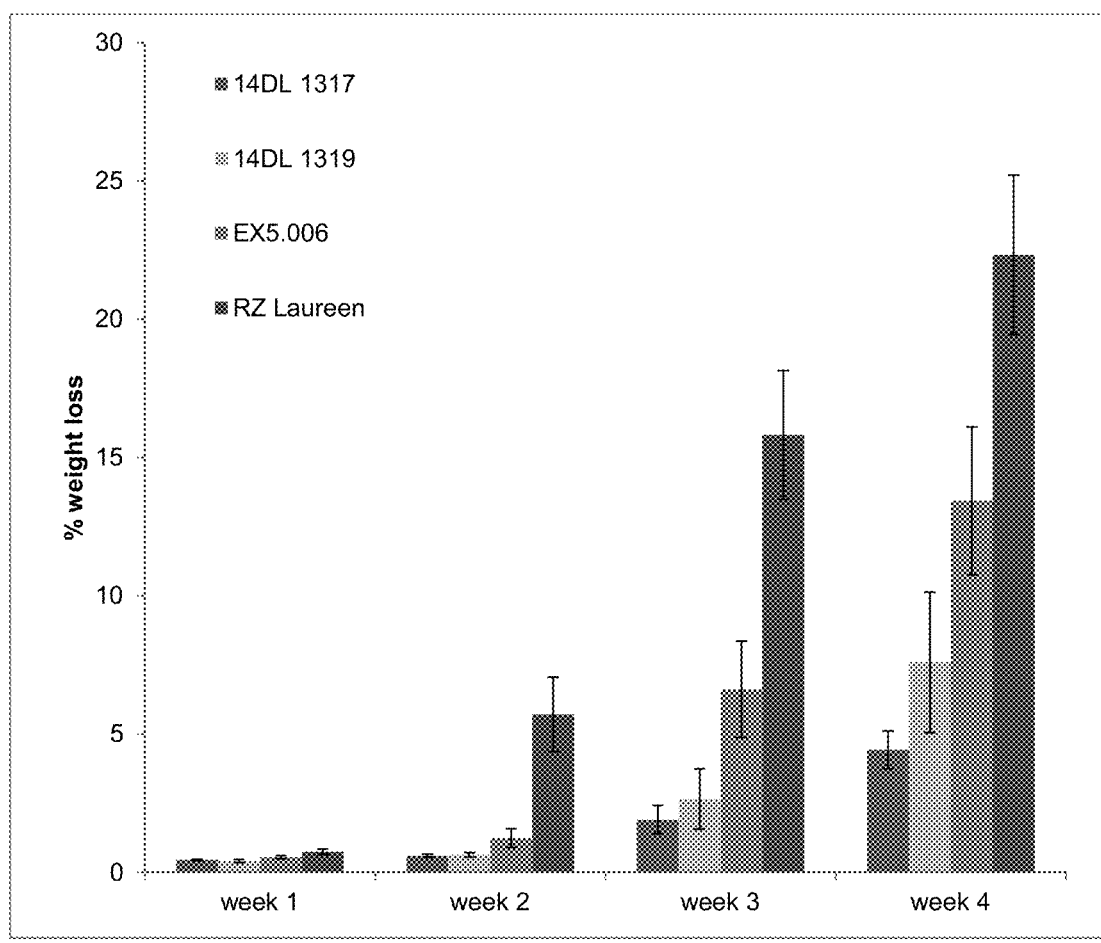
FIG. 8: Comparison liquid weight loss after a leakage test, in percentages.

The weight of the boxes was taken, an after that once a week the fruits in the net were removed, and the boxes with the leaked liquid were weighed. The difference determined the weight of the liquid lost by the fruits. Results in % weight loss are presented in FIG. 8.

It appeared that the fruits with the largest seed cavities also showed the biggest loss of liquid.

The invention is further described by the following numbered paragraphs:

1. Parthenocarpic cucumber fruit which carries a QTL that leads to a small seed cavity in a parthenocarpic fruit.
2. Parthenocarpic cucumber fruit of paragraph 1 which carries a QTL1 that leads to a small seed cavity, which QTL1 is located on chromosome 1 between marker sequences SEQ ID No. 1 and SEQ ID No. 2, preferably between marker sequences SEQ ID No. 9 and SEQ ID No. 2.
3. Parthenocarpic cucumber fruit of paragraph 1 or 2 which carries a QTL1 that leads to a small seed cavity, which QTL1 is as comprised in the genome of a cucumber plant representative seed of which was deposited with the NCIMB under deposit numbers NCIMB 42411 and NCIMB 42424 and NCIMB 42590, and is in particular located therein between marker sequences SEQ ID No. 1 and SEQ ID No. 2, more particular between marker sequences SEQ ID No. 9 and SEQ ID No. 2.
4. Parthenocarpic cucumber fruit of paragraph 1, 2 or 3, wherein the QTL is a QTL1, the presence of which QTL1 can be identified by any of the markers on chromosome 1 having SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, and/or SEQ ID No. 15, preferably by any of the markers on chromosome 1 having SEQ ID No. 10, SEQ ID No. 11, SEQ ID No. 12, SEQ ID No. 13, SEQ ID No. 14, and/or SEQ ID No. 15, or any combination of these SEQ ID Nos.
5. Parthenocarpic cucumber fruit of paragraph 1, which carries a QTL2 that leads to a small seed cavity, which QTL2 is located on chromosome 2 between marker sequences SEQ ID No. 16 and SEQ ID No. 17.
6. Parthenocarpic cucumber fruit of paragraph 1 or 5 which carries a QTL2 that leads to a small seed cavity, which QTL2 is as comprised in the genome of a cucumber plant representative seed of which was deposited with the NCIMB under deposit numbers NCIMB 42411 and NCIMB 42424 and NCIMB 42590, and is in particular located therein between marker sequences SEQ ID No. 16 and SEQ ID No. 17.
7. Parthenocarpic cucumber fruit of paragraph 1, 5 or 6, wherein the QTL is a QTL2, the presence of which QTL2 can be identified by any of the markers on chromosome 2 having SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, and/or SEQ ID No. 28, or any combination of these SEQ ID Nos.
8. Parthenocarpic cucumber fruit of paragraphs 1-7, comprising QTL1 and QTL2.
9. Parthenocarpic cucumber fruit of paragraphs 1-8, comprising QTL1 or QTL2 in heterozygous form; or comprising QTL1 in homozygous form, or QTL2 in homozygous form, or QTL1 and QTL2 in heterozygous form, or QTL1 in homozygous form and QTL2 in heterozygous form, or QTL2 in homozygous form and QTL1 in heterozygous form, or both QTL1 and QTL2 in homozygous form, which parthenocarpic fruits have a small seed cavity.

10. Parthenocarpic cucumber fruit of paragraphs 1-9, wherein a small seed cavity is a seed cavity of which the ratio of the surface area of the seed cavity in relation to the total surface area in cm² of a fruit cut in cross-section in order of increased preference is at least 5% smaller, 10% smaller, 15% smaller, 20% smaller, 23% smaller, 24% smaller when compared to the ratio of the seed cavity of a parthenocarpic fruit of a control plant, optionally an isogenic control plant, in relation to its total surface area in cm² of a fruit cut in cross-section.

11. Cucumber plant comprising QTL1 and/or QTL2 as of paragraphs 2-9, which cucumber plant is capable of producing parthenocarpic fruits that have a small seed cavity.

12. Part of a parthenocarpic cucumber fruit having a small seed cavity and comprising QTL1 and/or QTL2 of paragraphs 2-9, particularly a part that comprises a small seed cavity or a fragment thereof, optionally in processed form.

13. Marker for identification of a QTL1 which leads to a small seed cavity in a parthenocarpic cucumber fruit, which marker is selected from the group of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, and SEQ ID No. 15.

14. Marker for identification of a QTL2 which leads to a small seed cavity in a parthenocarpic cucumber fruit, which marker is selected from the group of SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, and SEQ ID No. 28.

15. Use of a marker for identification of a QTL1 which leads to a small seed cavity in a parthenocarpic cucumber fruit, which marker is selected from the group of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, and SEQ ID No. 15.

16. Use of a marker for identification of a QTL2 which leads to a small seed cavity in a parthenocarpic cucumber fruit, which marker is selected from the group of SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, and SEQ ID No. 28.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A parthenocarpic cucumber fruit which carries a genetic region that leads to a small seed cavity in the parthenocarpic fruit, wherein the genetic region is as in seed deposited with the NCIMB under deposit numbers NCIMB 42411 or NCIMB 42424 or NCIMB 42590, and said genetic region is located on chromosome 1 between marker sequences SEQ ID NO: 1 and SEQ ID NO: 2.

2. The parthenocarpic cucumber fruit as claimed in claim 1, wherein the presence of the genetic region can be identified by any of the markers on chromosome 1 having SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and/or SEQ ID NO: 15.

3. A parthenocarpic cucumber fruit which carries a genetic region that leads to a small seed cavity in a parthenocarpic fruit, wherein the genetic region is as in seed deposited with the NCIMB under deposit numbers NCIMB 42411 or NCIMB 42424 or NCIMB 42590, and said genetic region is located on chromosome 2 between marker sequences SEQ ID NO: 16 and SEQ ID NO: 17.

4. The parthenocarpic cucumber fruit as claimed in claim 3, wherein the presence of the genetic region can be identified by any of the markers on chromosome 2 having SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and/or SEQ ID NO: 28, or any combination of these SEQ ID numbers.

5. The parthenocarpic cucumber fruit as claimed in claim 1, further comprising the genetic region of claim 3.

6. A parthenocarpic cucumber fruit which carries a genetic region that leads to a small seed cavity in the parthenocarpic fruit, wherein the genetic region is as in seed deposited with the NCIMB under deposit numbers NCIMB 42411 or NCIMB 42424 or NCIMB 42590, and said genetic region is located on chromosome 1 between marker sequences SEQ ID NO: 1 and SEQ ID NO: 2[The parthenocarpic cucumber fruit as claimed in claim 1], comprising the genetic region[of claim 1] in heterozygous form; or the genetic region[of claim 1] in homozygous form, or the genetic region[of claim 1] and the genetic region of claim 3 in heterozygous form, or the genetic region[of claim 1] in homozygous form and the genetic region of claim 3 in heterozygous form, or the genetic region of claim 3 in homozygous form and the genetic region[of claim 1] in heterozygous form, or both the genetic region[of claim 1] and the genetic region of claim 3 in homozygousform, which parthenocarpic fruits have a small seed cavity.

7. The parthenocarpic cucumber fruit as claimed in claim 1 or 3, wherein a small seed cavity is a seed cavity of which the ratio of the surface area of the seed cavity in relation to the total surface area in $cm^2$ of a fruit cut in cross-section is at least 5% smaller when compared to the ratio of the seed cavity of a parthenocarpic fruit of a control plant, optionally an isogenic control plant, in relation to its total surface area in $cm^2$ of a fruit cut in cross-section.

8. The cucumber plant comprising the genetic region as defined in claim 1, which cucumber plant is capable of producing parthenocarpic fruits that have a small seed cavity.

9. A part of a parthenocarpic cucumber fruit having a small seed cavity and comprising any of the genetic regions of claim 6.

10. A method for identifying a genetic region which leads to a small seed cavity in a parthenocarpic cucumber fruit comprising determining the presence of a marker to identify the genetic region, which marker is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15.

11. A method for identifying a genetic region which leads to a small seed cavity in a parthenocarpic cucumber fruit comprising determining the presence of a marker to identify the genetic region, which marker is selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

12. The parthenocarpic cucumber fruit as claimed in claim 1, which carries genetic region that leads to a small seed cavity, which genetic region is located on chromosome 1 between marker sequences SEQ ID NO: 9 and SEQ ID NO: 2.

13. The parthenocarpic cucumber fruit as claimed in claim 1, wherein the genetic region can be identified by any of the markers on chromosome 1 having SEQ ID NO: 10, SEQ ID NO: 11, SEQ ID NO: 12, SEQ ID NO: 13, SEQ ID NO: 14, and/or SEQ ID NO: 15, or any combination of these SEQ ID numbers.

14. The parthenocarpic cucumber fruit as claimed in claim 1, wherein the genetic region is located in the genome of a cucumber plant representative seed of which was deposited with the NCIMB under deposit numbers NCIMB 42411 or NCIMB 42424 or NCIMB 42590 between marker sequences SEQ ID NO: 1 and SEQ ID NO: 2.

15. The parthenocarpic cucumber fruit as claimed in claim 1, wherein the genetic region is located in the genome of a cucumber plant representative seed of which was deposited with the NCIMB under deposit numbers NCIMB 42411 or NCIMB 42424 or NCIMB 42590 between marker sequences SEQ ID NO: 9 and SEQ ID NO: 2.

16. The parthenocarpic cucumber fruit as claimed in claim 1 or 3, wherein a small seed cavity is a seed cavity of which the ratio of the surface area of the seed cavity in relation to the total surface area in $cm^2$ of a fruit cut in cross-section is at least 10% smaller when compared to the ratio of the seed cavity of a parthenocarpic fruit of a control plant, optionally an isogenic control plant, in relation to its total surface area in $cm^2$ of a fruit cut in cross-section.

17. The parthenocarpic cucumber fruit as claimed in claim 1 or 3, wherein a small seed cavity is a seed cavity of which the ratio of the surface area of the seed cavity in relation to the total surface area in $cm^2$ of a fruit cut in cross-section is at least 15% smaller when compared to the ratio of the seed cavity of a parthenocarpic fruit of a control plant, optionally an isogenic control plant, in relation to its total surface area in $cm^2$ of a fruit cut in cross-section.

18. The parthenocarpic cucumber fruit as claimed in claim 1 or 3, wherein a small seed cavity is a seed cavity of which the ratio of the surface area of the seed cavity in relation to the total surface area in $cm^2$ of a fruit cut in cross-section is at least 20% smaller when compared to the ratio of the seed cavity of a parthenocarpic fruit of a control plant, optionally an isogenic control plant, in relation to its total surface area in $cm^2$ of a fruit cut in cross-section.

19. The parthenocarpic cucumber fruit as claimed in claim 1 or 3, wherein a small seed cavity is a seed cavity of which the ratio of the surface area of the seed cavity in relation to the total surface area in $cm^2$ of a fruit cut in cross-section is at least 23% smaller when compared to the ratio of the seed cavity of a parthenocarpic fruit of a control plant, optionally an isogenic control plant, in relation to its total surface area in cm² of a fruit cut in cross-section.

20. The parthenocarpic cucumber fruit as claimed in claim 1 or 3, wherein a small seed cavity is a seed cavity of which the ratio of the surface area of the seed cavity in relation to the total surface area in cm² of a fruit cut in cross-section is at least 24% smaller when compared to the ratio of the seed cavity of a parthenocarpic fruit of a control plant, optionally an isogenic control plant, in relation to its total surface area in cm² of a fruit cut in cross-section.

21. The parthenocarpic cucumber fruit as claimed in claim 3, wherein the genetic region is located in the genome of a cucumber plant representative seed of which was deposited with the NCIMB under deposit numbers NCIMB 42411 or NCIMB 42424 or NCIMB 42590 between marker sequences SEQ ID NO: 16 and SEQ ID NO: 17.

22. The part of the parthenocarpic cucumber fruit of claim 9, wherein the part comprises a small seed cavity or a fragment thereof, optionally in processed form.

23. A parthenocarpic cucumber fruit which carries a genetic region that leads to a small seed cavity in a parthenocarpic fruit, wherein the genetic region is as in seed deposited with the NCIMB under deposit numbers NCIMB 42411 or NCIMB 42424 or NCIMB 42593, and said genetic region is located on chromosome 2 between marker sequences SEQ ID NO: 16 and SEQ ID NO: 17[The parthenogeniccucumber fruit as claimed in claim 5], further comprising the genetic region of claim 1.

24. A parthenocarpic cucumber fruit which carries a genetic region that leads to a small seed cavity in a parthenocarpic fruit, wherein the genetic region is as in seed deposited with the NCIMB under deposit numbers NCIMB 42411 or NCIMB 42424 or NCIMB 42590, and said genetic region is located on chromosome 2 between marker sequences SEQ ID NO: 16 and SEQ ID NO: 17[The parthenogeniccucumber fruit as claimed in claim 5], comprising the genetic region[of claim 5] in heterozygous form; or the genetic region[of claim 5] in homozygous form, or the genetic region of claim 1 and the genetic region[of claim 5] in heterozygous form, or the genetic region of claim 1 in homozygous form and the genetic region[of claim 5] in heterozygous form, or the genetic region[of claim 5] in homozygous form and the genetic region of claim 1 in heterozygous form, or both the genetic region of claim 1 and the genetic region[of claim 5] in homozygous form, which parthenocarpic fruits have a small seed cavity.

25. The cucumber plant comprising the genetic region as defined in claim 3, which cucumber plant is capable of producing parthenocarpic fruits that have a small seed cavity.

26. A part of a parthenocarpic cucumber fruit having a small seed cavity and comprising any of the genetic regions of claim 24.

* * * * *

```
                          SEQUENCE LISTING

<160> NUMBER OF SEQ ID NOS: 28

<210> SEQ ID NO 1
<211> LENGTH: 108
<212> TYPE: DNA
<213> ORGANISM: Cucumis sativus
<220> FEATURE:
<221> NAME/KEY: source
<222> LOCATION: 1..108
<223> OTHER INFORMATION: /organism="Cucumis sativus"
      /mol_type="unassigned DNA"

<400> SEQUENCE: 1
actgagacat gcaggcagac ttgcgaagat mtagactcga gctttatcat tggcctttat      60
tcagcagtat acctaacagc ttggtatgca ttacgagcag gggctgta                  108

<210> SEQ ID NO 2
<211> LENGTH: 251
<212> TYPE: DNA
<213> ORGANISM: Cucumis sativus
<220> FEATURE:
<221> NAME/KEY: source
<222> LOCATION: 1..251
<223> OTHER INFORMATION: /organism="Cucumis sativus"
      /mol_type="unassigned DNA"

<400> SEQUENCE: 2
ctgcagccaa ctataaatga tatcactacc accacggttg agtgagcacg gagggactga      60
cgaaaccgag gcagctgact tctcaaggaa ctgcatctgc ttctcgtccg caatgcaaag     120
caaggaatca gtacatactt ctaaagccga tggtggcggg gttggcttga agtcctgaag     180
ctttgagtat tctgtgatga ggtgaaacat gtaagaatag actgtatcca tgctcaagyt     240
ctccatgaat t                                                          251

<210> SEQ ID NO 3
<211> LENGTH: 151
<212> TYPE: DNA
```

```
<213> ORGANISM: Cucumis sativus
<220> FEATURE:
<221> NAME/KEY: source
<222> LOCATION: 1..151
<223> OTHER INFORMATION: /organism="Cucumis sativus"
      /mol_type="unassigned DNA"

<400> SEQUENCE: 3
ttaaaaaaat aacttttatg aaagtagcaa aacaaagaaa mgttggagaa agtagtgctt      60
gcaagtttca ctctcgtttg gtctggattg ttgatacatc ttggcacatt tttatgcatg     120
gaaaaaaact tgagaataca ttatcctgca g                                    151

<210> SEQ ID NO 4
<211> LENGTH: 96
<212> TYPE: DNA
<213> ORGANISM: Cucumis sativus
<220> FEATURE:
<221> NAME/KEY: source
<222> LOCATION: 1..96
<223> OTHER INFORMATION: /organism="Cucumis sativus"
      /mol_type="unassigned DNA"

<400> SEQUENCE: 4
ttaagaacca caacacagta gccctggac gcacaaaaga aaatacaac agaagttgat       60 gcagaggaac atctacctgt ccctgcaggt ctcagt                                96

<210> SEQ ID NO 5
<211> LENGTH: 186
<212> TYPE: DNA
<213> ORGANISM: Cucumis sativus
<220> FEATURE:
<221> NAME/KEY: source
<222> LOCATION: 1..186
<223> OTHER INFORMATION: /organism="Cucumis sativus"
      /mol_type="unassigned DNA"

<400> SEQUENCE: 5
ttaatgaatc caaacagact ggaaaaatga ttatgttccc tgttactttt tctacagatt      60
cagatggggt tgtaccatta tgggatgcga tacttggtgg ccatgaggca gtagctcagc    120
tacttataga caatggtgct aaccttcggt caggagatgt cggccacttt gcgtgtactg    180
ctgcag                                                                186

<210> SEQ ID NO 6
<211> LENGTH: 80
<212> TYPE: DNA
<213> ORGANISM: Cucumis sativus
<220> FEATURE:
<221> NAME/KEY: source
<222> LOCATION: 1..80
<223> OTHER INFORMATION: /organism="Cucumis sativus"
      /mol_type="unassigned DNA"

<400> SEQUENCE: 6
tcttgatccc aactcaaagg tcctgatgca tgcaatgcct gaatagtgca acggtaggct      60
tgtaactcta acctatggat                                                  80

<210> SEQ ID NO 7
<211> LENGTH: 75
<212> TYPE: DNA
<213> ORGANISM: Cucumis sativus
<220> FEATURE:
<221> NAME/KEY: source
<222> LOCATION: 1..75
<223> OTHER INFORMATION: /organism="Cucumis sativus"
```

```
            /mol_type="unassigned DNA"

<400> SEQUENCE: 7
gcgtccatgc gaactcggtc acagagcatc tccttctgat gatagagaaa ggcgtaagtg      60
cagaaatact gagca                                                        75

<210> SEQ ID NO 8
<211> LENGTH: 251
<212> TYPE: DNA
<213> ORGANISM: Cucumis sativus
<220> FEATURE:
<221> NAME/KEY: source
<222> LOCATION: 1..251
<223> OTHER INFORMATION: /organism="Cucumis sativus"
            /mol_type="unassigned DNA"

<400> SEQUENCE: 8
ttaagagtca gtttggtgat agaaagaaga tccattggag gagctagaga atgatgtgta      60
tgggcataga ccttggtggg atgggttttc gtggtttggc ttccgttggt caatcaatgt     120
tggggtctcc ttttatggac tccaaatagc cttcttggtg taagtcgtta tgggtacaaa     180
cacaagtccc caaggaggc atctgtggca tccttggtgt cactcttgga gaggattggg     240
taatagaaaa g                                                          251

<210> SEQ ID NO 9
<211> LENGTH: 139
<212> TYPE: DNA
<213> ORGANISM: Cucumis sativus
<220> FEATURE:
<221> NAME/KEY: source
<222> LOCATION: 1..139
<223> OTHER INFORMATION: /organism="Cucumis sativus"
            /mol_type="unassigned DNA"

<400> SEQUENCE: 9
ctgcaggcat ctaagggagt ggtgagcgac aagatgttag ctattactcc ttccggcaga      60
gaggagaaat gggttcttcc ttctttaccc tccatgcttt tttttggtgt caagggatag     120
ttttatttat ttattttaa                                                  139

<210> SEQ ID NO 10
<211> LENGTH: 170
<212> TYPE: DNA
<213> ORGANISM: Cucumis sativus
<220> FEATURE:
<221> NAME/KEY: source
<222> LOCATION: 1..170
<223> OTHER INFORMATION: /organism="Cucumis sativus"
            /mol_type="unassigned DNA"

<400> SEQUENCE: 10
ttaacccggg caaacacctg gccaccttga acatatgctc gaggcaactg aaaggtgcaa      60
aaggtgagcg tttattggag gtgctcgtct tgggtacttg caaggcacaa agacctcacc     120
tcgcctctcg ctttaggcga gtgcccggct gcgcctcaac gacgctgcag                170

<210> SEQ ID NO 11
<211> LENGTH: 251
<212> TYPE: DNA
<213> ORGANISM: Cucumis sativus
<220> FEATURE:
<221> NAME/KEY: source
<222> LOCATION: 1..251
<223> OTHER INFORMATION: /organism="Cucumis sativus"
            /mol_type="unassigned DNA"
```

```
<400> SEQUENCE: 11
ttaacggtgt cagaaccaag aatagaggat tttgagccat ctgtcaaggt gacaaatggg      60
aaaaaggcgg gggacaatgg tgtaaaaaat aagctagaat tacctgtcat gtgaattgtg     120
gtaccaaagt ctatgaccca tttggtagat gatgtaagga gacactttgt attacctatg     180
tcagcggtgg aggcgatagg attagaggaa gatgacactt gcaatgaatc ttggtacatc     240
tgaaatttag c                                                          251

<210> SEQ ID NO 12
<211> LENGTH: 251
<212> TYPE: DNA
<213> ORGANISM: Cucumis sativus
<220> FEATURE:
<221> NAME/KEY: source
<222> LOCATION: 1..251
<223> OTHER INFORMATION: /organism="Cucumis sativus"
      /mol_type="unassigned DNA"

<400> SEQUENCE: 12
ttaagaaaat tggaaagaga tcaaaatcag ctgagttcta aaagatagta ttttcggtga      60
acctgggagt tagaggatat tttatataag cccttatact tgataatgga agttgaaatg     120
gaccttcaac aaaagttggg ttgaggttcc catcatactc aaacttgcta aacaggagct     180
gcacatgatt atgaagtgca tgtgaaaaac accatgcaag ggagaaatg agaagaaact      240 aaaagaaaag c                                                          251

<210> SEQ ID NO 13
<211> LENGTH: 79
<212> TYPE: DNA
<213> ORGANISM: Cucumis sativus
<220> FEATURE:
<221> NAME/KEY: source
<222> LOCATION: 1..79
<223> OTHER INFORMATION: /organism="Cucumis sativus"
      /mol_type="unassigned DNA"

<400> SEQUENCE: 13 tgcttttcc aggtgcattg cccattcagt tttcactgat gaagtacagt cttgcatggt       60
ggacattttc ctgctgcag                                                   79

<210> SEQ ID NO 14
<211> LENGTH: 213
<212> TYPE: DNA
<213> ORGANISM: Cucumis sativus
<220> FEATURE:
<221> NAME/KEY: source
<222> LOCATION: 1..213
<223> OTHER INFORMATION: /organism="Cucumis sativus"
      /mol_type="unassigned DNA"

<400> SEQUENCE: 14
ctgcaggggt tgcaacagct cctcctgtaa ttgcgtcgat aacaactttg tctcggttgt      60
tgttgctcgc agctgatact agagctcccg tcaaagcacc tccaatcatt gcattttttct    120 ggaaacaaat gttcgaatat atggaaaata ttcccaaaca aacatagaga gctggaagca    180
ctaatctaac agaatagctt gaacttgatt taa                                  213

<210> SEQ ID NO 15
<211> LENGTH: 187
<212> TYPE: DNA
<213> ORGANISM: Cucumis sativus
```

```
<220> FEATURE:
<221> NAME/KEY: source
<222> LOCATION: 1..187
<223> OTHER INFORMATION: /organism="Cucumis sativus"
      /mol_type="unassigned DNA"

<400> SEQUENCE: 15
ttaatacaat ccctatgaaa aaaatggcca caattctcaa ttactccaca aatctcctct        60
tccccaaatc cctcaataca tatcgcacac ttcctcccat cgcaatcccc aatttccct       120 gtttttattt ctctaaaacc catcttcacg gctgccggaa tttcctccga cgtctcctcc      180
gctgcag                                                                187

<210> SEQ ID NO 16
<211> LENGTH: 290
<212> TYPE: DNA
<213> ORGANISM: Cucumis sativus
<220> FEATURE:
<221> NAME/KEY: source
<222> LOCATION: 1..290
<223> OTHER INFORMATION: /organism="Cucumis sativus"
      /mol_type="unassigned DNA"

<400> SEQUENCE: 16
gaagacacaa gagctgatat tatccaatat ctctgtggaa gaaattattg taatagattg        60
gagaggcaat ggccagactc ataattacct gcaacatttg gagattcttt caagttgggg      120
tcttcatttg cttcttgttt aacccattca tttcttcgac tggaggtttc tcatctgtct      180
ttaaatttgt tatagatttg gacatagttt gttttctctc atctttgtat ttctacttct      240
ctagacttta cctagttacg gagctttcca tagagatgca tctttaccta                 290

<210> SEQ ID NO 17
<211> LENGTH: 251
<212> TYPE: DNA
<213> ORGANISM: Cucumis sativus
<220> FEATURE:
<221> NAME/KEY: source
<222> LOCATION: 1..251
<223> OTHER INFORMATION: /organism="Cucumis sativus"
      /mol_type="unassigned DNA"

<400> SEQUENCE: 17
ttaaatcaaa cccattatca gggacaacac caccttccaa taaagaactt ctaaaagcag        60
attgccaagc attcaaaatt ggttgagata caacagtttc ttcaacccat tcataagcct      120
tctcaaccaa ttccatgtcc caatcaacac ctgcacttgc aaaaaactct ttatgtcccc      180
tcgaatagaa cccggcattg accatgcttc ctccgccaag gactcgtcct cgtatgttct      240
ctacgccatc c                                                           251

<210> SEQ ID NO 18
<211> LENGTH: 78
<212> TYPE: DNA
<213> ORGANISM: Cucumis sativus
<220> FEATURE:
<221> NAME/KEY: source
<222> LOCATION: 1..78
<223> OTHER INFORMATION: /organism="Cucumis sativus"
      /mol_type="unassigned DNA"

<400> SEQUENCE: 18
aaacgacaaa gtgtgtggct tttgcctccg cgcctgatat tctcattgaa ttagaatttg        60
gggtgtttcc gttcgttg                                                     78
```

<210> SEQ ID NO 19
<211> LENGTH: 89
<212> TYPE: DNA
<213> ORGANISM: Cucumis sativus
<220> FEATURE:
<221> NAME/KEY: source
<222> LOCATION: 1..89
<223> OTHER INFORMATION: /organism="Cucumis sativus"
  /mol_type="unassigned DNA"

<400> SEQUENCE: 19
ctgcagcagc gaaggtcgag caaatgtgta aagragtcga gcgacaacaa agcttatctt    60
cggatttcaa tgtcgaaagt ggtgaactc                                      89

<210> SEQ ID NO 20
<211> LENGTH: 75
<212> TYPE: DNA
<213> ORGANISM: Cucumis sativus
<220> FEATURE:
<221> NAME/KEY: source
<222> LOCATION: 1..75
<223> OTHER INFORMATION: /organism="Cucumis sativus"
  /mol_type="unassigned DNA"

<400> SEQUENCE: 20
tcaggatgat aataataatc tccccaaaga cgggtagcga acttatcagc atcaaaaggg    60
attccatgaa gtttg                                                     75

<210> SEQ ID NO 21
<211> LENGTH: 76
<212> TYPE: DNA
<213> ORGANISM: Cucumis sativus
<220> FEATURE:
<221> NAME/KEY: source
<222> LOCATION: 1..76
<223> OTHER INFORMATION: /organism="Cucumis sativus"
  /mol_type="unassigned DNA"

<400> SEQUENCE: 21
gtatgctttt ttgtgtgctc tttggattgt attccctgaa tctccactta gctcgatgca    60
aaattttctt cttgtt                                                    76

<210> SEQ ID NO 22
<211> LENGTH: 251
<212> TYPE: DNA
<213> ORGANISM: Cucumis sativus
<220> FEATURE:
<221> NAME/KEY: source
<222> LOCATION: 1..251
<223> OTHER INFORMATION: /organism="Cucumis sativus"
  /mol_type="unassigned DNA"

<400> SEQUENCE: 22
tttaatcaaa atgatgcata taggaagaat gcatcataca cattgccaat ggaactctta    60
ggatattcaa aatgatagat agctaaatgt ggctttggct tggattgaaa agcagcagtt   120
ttgaaacaga catctgttgt tcatgaagtg ttattgtttt gttgaatgtt gtctctatca   180
gctccaaatt gattcttttt tcgttatatg cattagtgtg gtcggagata catgtgttgc   240
aatggaagat t                                                        251

<210> SEQ ID NO 23
<211> LENGTH: 80
<212> TYPE: DNA
<213> ORGANISM: Cucumis sativus

```
<220> FEATURE:
<221> NAME/KEY: source
<222> LOCATION: 1..80
<223> OTHER INFORMATION: /organism="Cucumis sativus"
      /mol_type="unassigned DNA"

<400> SEQUENCE: 23
cagcagatac catacctgct ccttcgcact tattccaaca acatccatag ctcttctagt      60
ggcaagatag tcatgagcat                                                  80

<210> SEQ ID NO 24
<211> LENGTH: 298
<212> TYPE: DNA
<213> ORGANISM: Cucumis sativus
<220> FEATURE:
<221> NAME/KEY: source
<222> LOCATION: 1..298
<223> OTHER INFORMATION: /organism="Cucumis sativus"
      /mol_type="unassigned DNA"
<220> FEATURE:
<221> NAME/KEY: misc_feature
<222> LOCATION: 30
<223> OTHER INFORMATION: /note="n = a, g, c or t"

<400> SEQUENCE: 24
gatcggatta tatttgaaag aaataatatn tacttaccaa gagaaaattt gaacatgttc      60
tccaaagctt gaagaaggtc aggatatcct tgatagatct taagatcaac tttcctaaga    120
aatggagctc catccatgct cactttatg aacattccgg ccgccgtctc ctcttttttc     180
tttgcttgta aagaattctt tcgaaatgat ctcaccggtg gccacccac aacttgtgcc     240 ctattaaata taaatatttt ctgtcaaatt ctaatttaag aagaaaaaaa accccaaa      298

<210> SEQ ID NO 25
<211> LENGTH: 454
<212> TYPE: DNA
<213> ORGANISM: Cucumis sativus
<220> FEATURE:
<221> NAME/KEY: source
<222> LOCATION: 1..454
<223> OTHER INFORMATION: /organism="Cucumis sativus"
      /mol_type="unassigned DNA"
<220> FEATURE:
<221> NAME/KEY: misc_feature
<222> LOCATION: 40,204,252,397
<223> OTHER INFORMATION: /note="n = a, g, c or t"

<400> SEQUENCE: 25
ttgcctgaaa aaacattcaa agaaagaaaa catcaataan ttttcatcat taaagagaga      60
gatctcaaga tctaattaag agatcggatt atatttgaaa gaataatat gtacttacca    120 agagaaaatt tgaacatgtt ctccaaagct tgaagaaggt caggatatcc ttgatagatc    180
ttaagatcaa ctttcctaag aaanggagct ccatccatgc tcactttat gaacattccg     240 gccgccgtct cntcttttc tttgcttgta aagaattctt tcgaaatgat ctcaccggtg    300 gccacccac aacttgtgcc ctattaaata taaatatttt ctgtcaaatt ctaatttaag    360
aagaaaaaaa accccaaaat ctaactaatt tctaaanttt tagaaataat aaaccaaaac    420
tttactgttt gataaaagtt cttacttggt agga                                454

<210> SEQ ID NO 26
<211> LENGTH: 685
<212> TYPE: DNA
<213> ORGANISM: Cucumis sativus
<220> FEATURE:
<221> NAME/KEY: source
```

```
<222> LOCATION: 1..685
<223> OTHER INFORMATION: /organism="Cucumis sativus"
      /mol_type="unassigned DNA"
<220> FEATURE:
<221> NAME/KEY: misc_feature
<222> LOCATION: 12
<223> OTHER INFORMATION: /note="n = a, g, c or t"

<400> SEQUENCE: 26
atgtgtcttc antgatggta ctgttttgat tcccataaac atttgggtca agcttacttg      60
ttggtggaaa aacctatata taattaatat aaattgagat taattagaat cttttggtaa     120
aaaaaatcat ttgagaaaat tgagactaat tatttgttaa aatcattact tcaagacgac     180
gaatcaatag aggattgggt cctgctaaca tttctcttgc aaattcttca tcagtgctcc     240
atcctatttt attatctgtt caaaattaat tgtaaattaa ttaagtatga tcaacaaaat     300
tgtataaaca attaatgtta gtatattcat tcctcataat atctaaattt ttgtaccttt     360
gacaacttcg ggagtaggaa atttgaggaa ttttcacca tcattcctca cgagtgcttt      420
gaacaaaggt ggagtgaggt cctcagtgag ggtcttaaaa gcattaaatg gaatgggaaa     480
acctctctca aagagattat caacttcttt aaaattgtca aattcatttg gagttacatc     540
aaatatggat tgaagtcctg gtttgattga tatcgaaagt gcttttaatg tataaccaag     600
gaaatctgac atcttcaaat gcccaaagtt ttcatctttt ggtacataga tgtctaagct     660
cattattggt gacaatctgc tctca                                           685

<210> SEQ ID NO 27
<211> LENGTH: 225
<212> TYPE: DNA
<213> ORGANISM: Cucumis sativus
<220> FEATURE:
<221> NAME/KEY: source
<222> LOCATION: 1..225
<223> OTHER INFORMATION: /organism="Cucumis sativus"
      /mol_type="unassigned DNA"

<400> SEQUENCE: 27
ttaatgatgc tatcttccgt ttttccttag atcttgaaga gcgtatacta aagcagcaac      60
aagaagaaga acaacgaaar cgcgagcgtc gagaaaggaa gaaagaaaag aaggttagta     120
ctataataac ctcatgattt tggcaacaat ttctatcatg aaaagwgggg atcacatctt     180
acacttgtgt ttattctcct ggaatgtaga aagagaaggc tgcag                     225

<210> SEQ ID NO 28
<211> LENGTH: 156
<212> TYPE: DNA
<213> ORGANISM: Cucumis sativus
<220> FEATURE:
<221> NAME/KEY: source
<222> LOCATION: 1..156
<223> OTHER INFORMATION: /organism="Cucumis sativus"
      /mol_type="unassigned DNA"

<400> SEQUENCE: 28
ttaatacttt cttgctttca cttgttctcg attcagaatt agaagactct scctccgata      60
tccaattcta tacacagcat ctaatccggg agctcggacg tgaaacgtac atcgggcaac     120
gtgcaatagt ttctgtgtct caaagaattg ctgcag                               156
```